(12) United States Patent
Kawahara et al.

(10) Patent No.: US 10,481,125 B2
(45) Date of Patent: Nov. 19, 2019

(54) BIOMOLECULE MEASURING DEVICE

(71) Applicant: HITACHI HIGH-TECHNOLOGIES CORPORATION, Tokyo (JP)

(72) Inventors: Takayuki Kawahara, Tokyo (JP); Yoshimitsu Yanagawa, Tokyo (JP); Naoshi Itabashi, Tokyo (JP); Riichiro Takemura, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 220 days.

(21) Appl. No.: 15/026,657

(22) PCT Filed: Oct. 2, 2014

(86) PCT No.: PCT/JP2014/076446
§ 371 (c)(1),
(2) Date: Apr. 1, 2016

(87) PCT Pub. No.: WO2015/050225
PCT Pub. Date: Apr. 9, 2015

(65) Prior Publication Data
US 2016/0245777 A1    Aug. 25, 2016

(30) Foreign Application Priority Data

Oct. 4, 2013 (JP) .................................. 2013-209073

(51) Int. Cl.
*G01N 27/414* (2006.01)
(52) U.S. Cl.
CPC ................................ *G01N 27/4145* (2013.01)
(58) Field of Classification Search
CPC ............. G01N 27/4145; G01N 27/414; G01N 27/4141; G01N 27/4148
(Continued)

(56) References Cited

U.S. PATENT DOCUMENTS 4,743,954 A * 5/1988 Brown ............... G01N 27/4148
257/253
7,948,015 B2 * 5/2011 Rothberg ............. C12Q 1/6874
257/253
(Continued)

FOREIGN PATENT DOCUMENTS

JP      2010-513869 A    4/2010
JP      2013-533482 A    8/2013
JP      2014-115125 A    6/2014

OTHER PUBLICATIONS

Georgiou, P. et al. (2009). "ISFET Threshold Voltage Programming in CMOS using Hot-Electron Injection." Electronic Letters. 45(22).*
(Continued)

*Primary Examiner* — Jill A Warden
*Assistant Examiner* — Jacqueline Brazin
(74) *Attorney, Agent, or Firm* — Baker Botts L.L.P.

(57) ABSTRACT

To a biomolecule measuring apparatus, a semiconductor sensor for detecting ions generated by a reaction between a biomolecular sample and a reagent is set. The semiconductor sensor has a plurality of cells which are arranged on a semiconductor substrate, and each of which detects ions, and a plurality of readout wires. Each of the plurality of cells has an ISFET which has a floating gate and which detects ions, a first MOSFET M2 for amplifying an output from the ISFET, and a second MOSFET M3 which selectively transmits an output from the first MOSFET to a corresponding readout wire R1. Each of the plurality of cells is provided with a third MOSFET M1 which generates hot electrons in the ISFET and which injects a charge to the floating gate of the ISFET. Here, the second MOSFET and the third MOSFET are separately controlled.

12 Claims, 20 Drawing Sheets

(58) Field of Classification Search
USPC .................................................... 422/82.03
See application file for complete search history.

(56) References Cited

U.S. PATENT DOCUMENTS

| | | |
|---|---|---|
| 2008/0094074 A1 | 4/2008 | Kim et al. |
| 2010/0301398 A1 | 12/2010 | Rothberg et al. |
| 2011/0299337 A1* | 12/2011 | Parris .................. G05F 1/575 |
| | | 365/185.18 |
| 2012/0000274 A1 | 1/2012 | Fife |
| 2013/0187572 A1* | 7/2013 | Grajcar .............. H05B 33/0824 |
| | | 315/312 |

OTHER PUBLICATIONS

International Search Report, dated Jan. 6, 2015, which issued during the prosecution of International Patent Application No. PCT/JP2014/076446, which corresponds to the present application.

Liu et al., "An Extended CMOS ISFET Model Incorporating the Physical Design Geometry and the Effects on Performance and Offset Variation", IEEE Transactions Electron Devices, vol. 58, No. 12, Dec. 2011, pp. 4414-4422.

Milgrew et al., "Matching the Transconductance Characteristics of CMOS ISFET Arrays by Removing Trapped Charge", IEEE Transactions Electron Devices, vol. 55, No. 4, Apr. 2008, pp. 1074-1079.

Georgiou, et al., "ISFET threshold voltage programming in CMOS using hot-electron injection", Electronics Letters, vol. 45, No. 22, Oct. 2009, 2 pages.

\* cited by examiner

FIG. 17
(A)
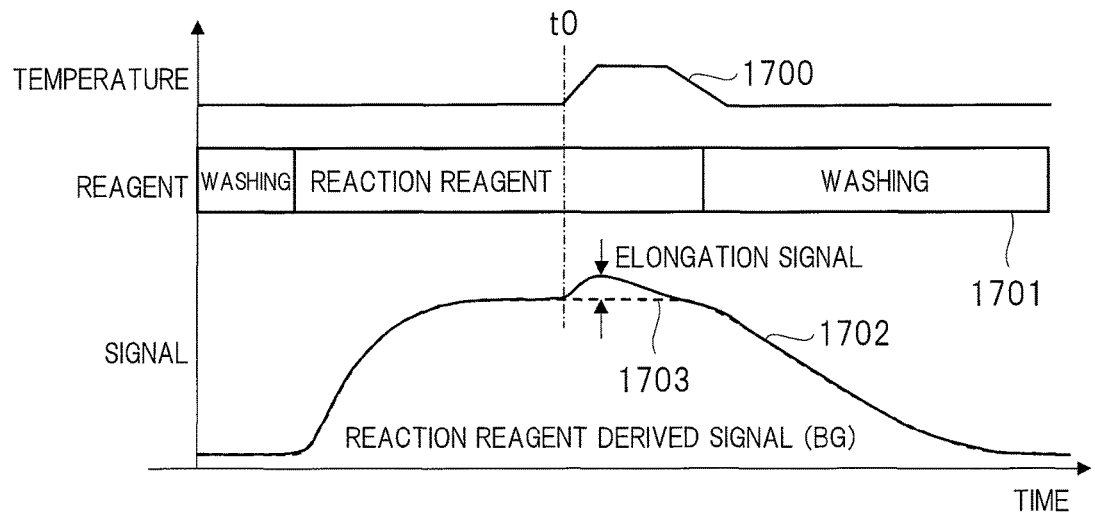
(B)
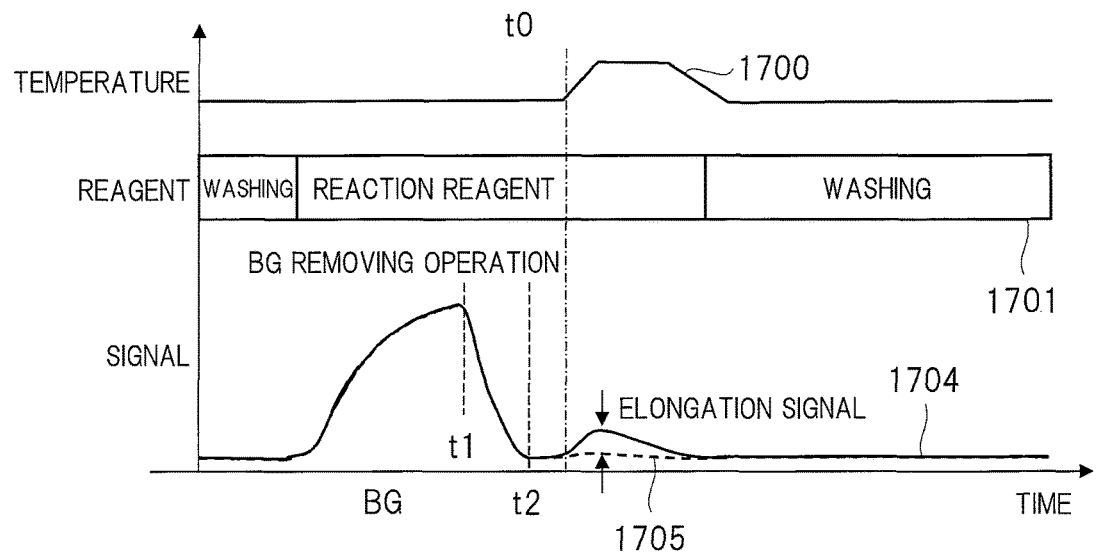

(A) INCREASE IN DIAGNOSTIC REGION IS SUPPORTED BY INCREASE IN TYPES OF CHIP (B) INCREASE IN DIAGNOSTIC REGION IS SUPPORTED BY SOFTWARE REWRITING

BIOMOLECULE MEASURING DEVICE

CROSS REFERENCE TO PRIOR APPLICATIONS

This application is a U.S. National Phase application under 35 U.S.C. § 371 of International Application No. PCT/JP2014/076446, filed on Oct. 2, 2014, and claims benefit of priority to Japanese Patent Application No. 2013-209073, filed on Oct. 4, 2013. The International Application was published in Japanese on Apr. 9, 2015 as WO 2015/050225 A1 under PCT Article 21(2). The contents of the above applications are hereby incorporated by reference.

TECHNICAL FIELD

The present invention relates to a biomolecule measuring apparatus, and, more particular, the present invention relates to a biomolecule measuring apparatus using a semiconductor technique.

BACKGROUND ART

In recent years, a biomolecule measuring device using a semiconductor technique has been focused on attention. Patent Document 1 has described a DNA sequencer that determines a base sequence of a deoxyribonucleic acid (DNA) at high speed and low cost by using a pH sensor array (semiconductor sensor) manufactured by the semiconductor technique. The semiconductor sensor can quantify a reaction between a target biomolecular sample and a reagent by using the strength of an electric signal. For this reason, this method is advantageous in terms of costs without the necessity of an expensive fluorescent reagent as conventionally used. Moreover, since sensors of several millions to several hundred millions can be integrated on a single semiconductor substrate by a micro-processing technique of a semiconductor and can measure in parallel, the throughput of the measurement can be easily improved.

One of the semiconductor sensors that are particularly used so often in the field of the biomolecule measuring device is an ion sensitive field effect transistor (Ion Sensitive Field Effect Transistor: hereinafter, referred to as ISFET). The ISFET is a device for measuring an interface electric potential induced on an ion sensitive layer.

In Patent Document 1, by using the ISFET, a change in the hydrogen ion concentration caused by an elongation reaction of DNA due to the reagent is measured. There are four types of bases forming the DNA, and the type of the base can be specified from the change in the hydrogen ion concentration by using a reagent that reacts only with a specific base to generate hydrogen ions. Here, the four types of bases are adenine, thymine, cytosine and guanine.

The voltage change due to a change in hydrogen ion concentration can be theoretically found from an equation referred to as Nernst equation. For example, at 25° C., the voltage change is about 59 mV/pH. This change (variation) changes the gate voltage of the ISFET so that the output current of the ISFET changes. Practically, the voltage change with respect to the change in the hydrogen ion concentration is lower than its theoretical value, and becomes about several 10 mV per pH. The change in hydrogen ion concentration caused by the above-described elongation reaction of DNA is about 0.1 mV in terms of the pH change, although it also depends on the number of DNA chains causing the reaction, the size of space causing the reaction, and the reagent. Therefore, the change in the output signal of the ISFET is extremely small.

In order to solve this problem, increase in the sensitivity of the ISFET has been studied. As an example of this, a technique described in Patent Document 2 is cited. In Patent Document 2, a large number of ISFETs are arranged in an array form, and FIG. 75F of the document shows a unit cell for detecting the change in the hydrogen ion concentration by a reference numeral 75F1. This unit cell 75F1 has a function of increasing the sensitivity. In FIG. 75F, a portion indicated as ISFET represents an ISFET circuit, and the ISFET is configured by an ion sensitive layer (portion) 75F6 and an MOSFET (transistor) 75F2 whose gate is connected with the ion sensitive layer. In this drawing, a reference numeral 75F3 indicates an MOSFET to which a bias current is applied, and a reference numeral 75F4 is an MOSFET to be connected to an output signal wire 75F7 (Column Bus). Moreover, in this drawing, "Row Select" represents a signal wire for use in selecting the unit cell 75F1.

In Patent Document 2, the sensitivity of the ISFET is increased by the MOSFET 75F5. That is, the output of the MOSFET 75F2 is inputted to the gate of the MOSFET 75F5. By the change in the hydrogen ion concentration, the gate voltage of an ISFET configured by the MOSFET 75F2 and the ion sensitive layer 75F6 is changed. By this change, the output current of the ISFET is changed. This change is amplified once by the MOSFET 75F5. That is, the small change in the ISFET output current due to the change in hydrogen ion concentration is amplified. After the amplification, the resulting current is outputted to an output signal line 75F7 through the MOSFET 75F4. Thus, the sensitivity of the ISFET can be increased.

Meanwhile, existence of a charge other than being derived from the measurement target ion in the device of the ISFET causes a measurement error. In general, the semiconductor process has such a problem that a charge tends to be easily accumulated in the device since a plasma processing and an ion injection are performed at the time of manufacturing a device. In relation to this problem, Non-Patent Document 1 has described that charges are accumulated on interfaces among an ion sensitive layer, a protective layer and electrodes as well as on a floating electrode and a gate oxide film. Non-Patent Document 1 has described that the threshold voltage of the ISFET is offset by about ±10 V due to such charge accumulation.

If such an offset exists, the offset is also amplified as it is in the configuration as shown in FIG. 75F of Patent Document 2.

As a conventional technique for removing such an offset, Patent Document 1 has described a method of extracting the charge to the outside of the device by giving an energy thereto by irradiating it with ultraviolet rays. Moreover, Non-Patent Document 2 has described that the irradiation with ultraviolet rays needs to be performed for a long period of time such as 10 hours. Furthermore, as another method, Non-Patent Document 3 has described that the change in the threshold voltage due to the captured charges can be reduced by injection of hot electrons.

RELATED ART DOCUMENTS

Patent Documents

Patent Document 1: Japanese Patent Application Laid-Open Publication No. 2010-513869

Patent Document 2: U.S. Patent Application Laid-Open Publication No. 2010/0301398A1

Non-Patent Documents

Non-Patent Document 1: "An Extended CMOS ISFET Model Incorporating the Physical Design Geometry and the Effects on Performance and Offset Variation", Liu, et. al, IEEE Trans. Elec. Dev, December, 2011

Non-Patent Document 2: "Matching the Transconductance Characteristics of CMOS ISFET Arrays by Removing Trapped Charge", Milgrew, et. Al, IEEE Elec. Dev., April 2008

Non-Patent Document 3: "ISFET threshold voltage programming in CMOS using hot-electron injection", Georgiou, et. Al, Electronics Lett. October 2009

SUMMARY OF THE INVENTION

Problems to be Solved by the Invention

When a MOSFET having an amplifying function is inserted in order to increase the sensitivity of the ISFET, the large offset of the ISFET is also amplified. For this reason, it becomes difficult to detect the original change in hydrogen ion concentration (change in pH). Moreover, in the technique for discharging charges by the irradiation of ultraviolet rays, it is required to irradiate the ultraviolet rays for a long period of time, which results in a risk of damage of the biomolecules serving as a simple. In Non-Patent Document 3, with respect to the method for reducing the offset, injection of hot electrons to a single ISFET has been studied. However, particularly, a method suitable for a biomolecule measuring device having a plurality of ISFETs arranged in an array form has not been studied at all.

An object of the present invention is to provide a highly sensitive biomolecule measuring device having a plurality of ISFETs.

The above and other object and novel characteristics of the present invention will be apparent from the description of the present specification and the accompanying drawings.

Means for Solving the Problems

The typical summary of the inventions disclosed in the present application will be briefly described as follows.

That is, in the biomolecule measuring device, a semiconductor sensor for detecting ions generated by a reaction between a biomolecular sample and a reagent is set. This semiconductor sensor has a plurality of cells which are arranged in an array form and each of which detects ions, and a plurality of readout wires which are arranged in an array, on a semiconductor substrate. Each of the plurality of cells arranged in the array form includes an ISFET which has a floating gate and which detects the change in ion concentration, includes a first MOSFET which has a gate for receiving the output of the ISFET and which amplifies the output of the ISFET, and includes a second MOSFET which selectively transmits the output of the first MOSFET to the corresponding readout wire of the plurality of readout wires. Moreover, each of the plurality of cells is provided with a third MOSFET which is connected to the ISFET, which generates hot electrons (hot carriers) in the ISFET, and which injects a charge to the floating gate of the ISFET. Here, the second MOSFET and the third MOSFET can be controlled separately from each other.

By controlling the second MOSFET, the output of the ISFET amplified by the first MOSFET can be read. For example, based on the read output, the third MOSFET is controlled. By controlling the third MOSFET, hot electrons (hot carriers) are generated in the ISFET, and the generated charge can be injected to the floating gate of the ISFET. Thus, based on the read output, the threshold voltage of the ISFET can be set. In this manner, by setting the threshold voltage of the ISFET in each of the plurality of cells arranged in the array form, variation in the threshold voltage generated by the accumulated charge at the time of a manufacturing process or others can be reduced among the plurality of ISFETs, so that a highly sensitive biomolecule measuring device can be obtained.

In one embodiment, the biomolecule measuring device has a first operation mode which causes an electron tunneling current to flow from the floating gate of the ISFET of each of the plurality of cells to the semiconductor substrate. By executing the first operation mode, the threshold voltage of each of the plurality of ISFETs is changed toward a predetermined direction (to a high direction or a low direction). Thus, the threshold voltages of the plurality of ISFETs can be unified.

Moreover, in one embodiment, the biomolecule measuring device alternately performs an operation for injecting a charge to the floating gate of the ISFET by controlling the third MOSFET and an operation for transmitting the output of the ISFET to a readout wire by controlling the second MOSFET so as to determine whether or not the threshold voltage of the ISFET is within a predetermined range, so that the threshold voltage of the ISFET in each of the plurality of cells is within a predetermined range.

Furthermore, in one embodiment, before the operation for injecting a charge to the floating gate of the ISFET, the above-described first operation mode is executed. In this manner, the threshold voltage of each of the ISFETs is controlled to be within the predetermined range after the change of the threshold voltage of each of the plurality of ISFETs toward the predetermined direction, and therefore, the threshold voltage of each ISFET can be within a predetermined range more accurately.

Effects of the Invention

The effects obtained by typical aspects of the present invention will be briefly described below.

a highly sensitive biomolecule measuring device can be provided.

BRIEF DESCRIPTIONS OF THE DRAWINGS

FIG. 1 is a circuit diagram showing a configuration of a cell according to a first embodiment;

FIG. 2(A) and FIG. 2(B) are schematic views for explaining a scheme for cancelling an offset;

FIG. 3(A) to FIG. 3(G) are waveform diagrams showing operations in the first embodiment;

FIG. 4(A) to FIG. 4(E) are waveform diagrams showing another operations in the first embodiment;

Figure 18:
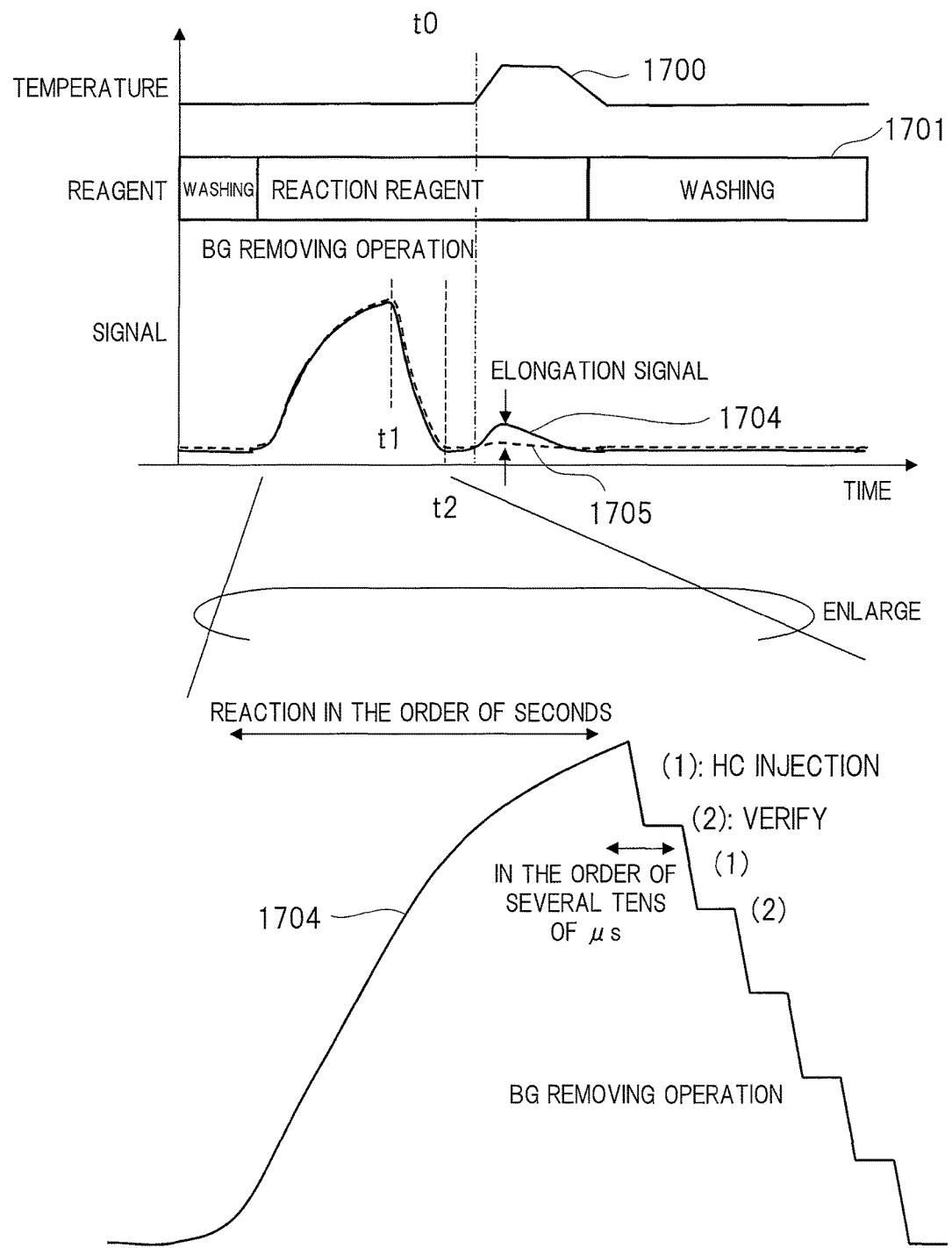
Figure 19:
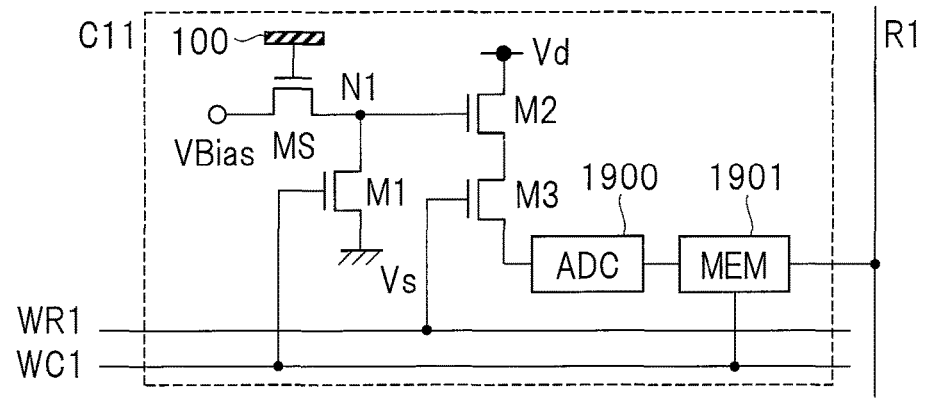
Figure 20:
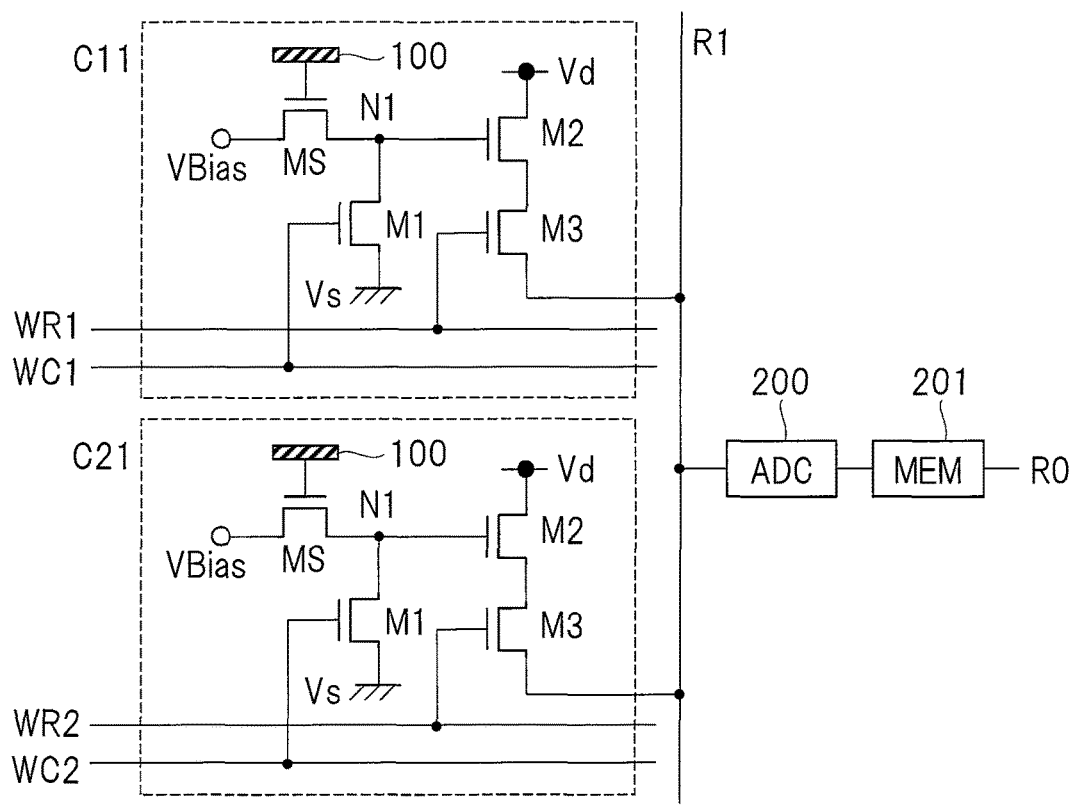
Figure 21:
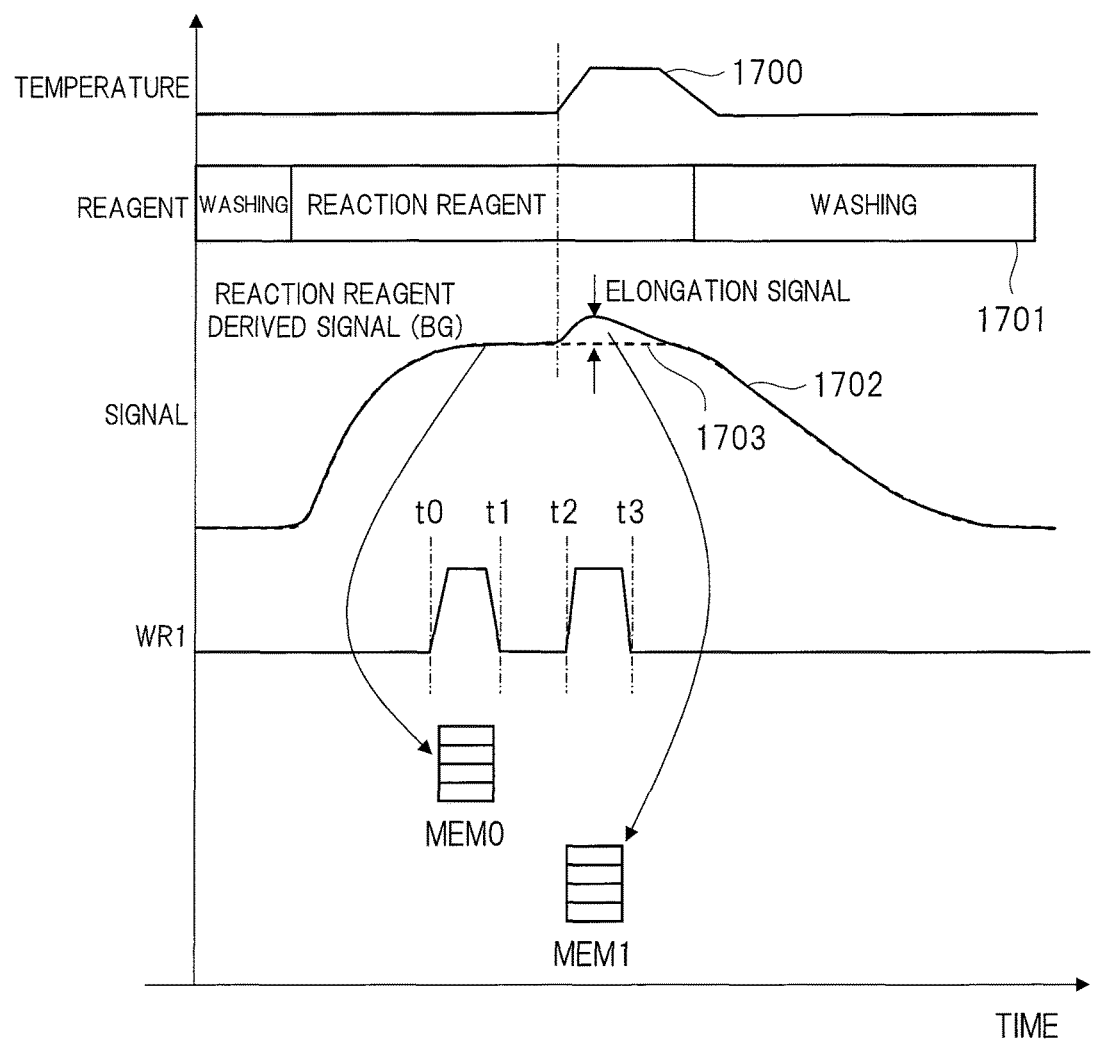
Figure 22:
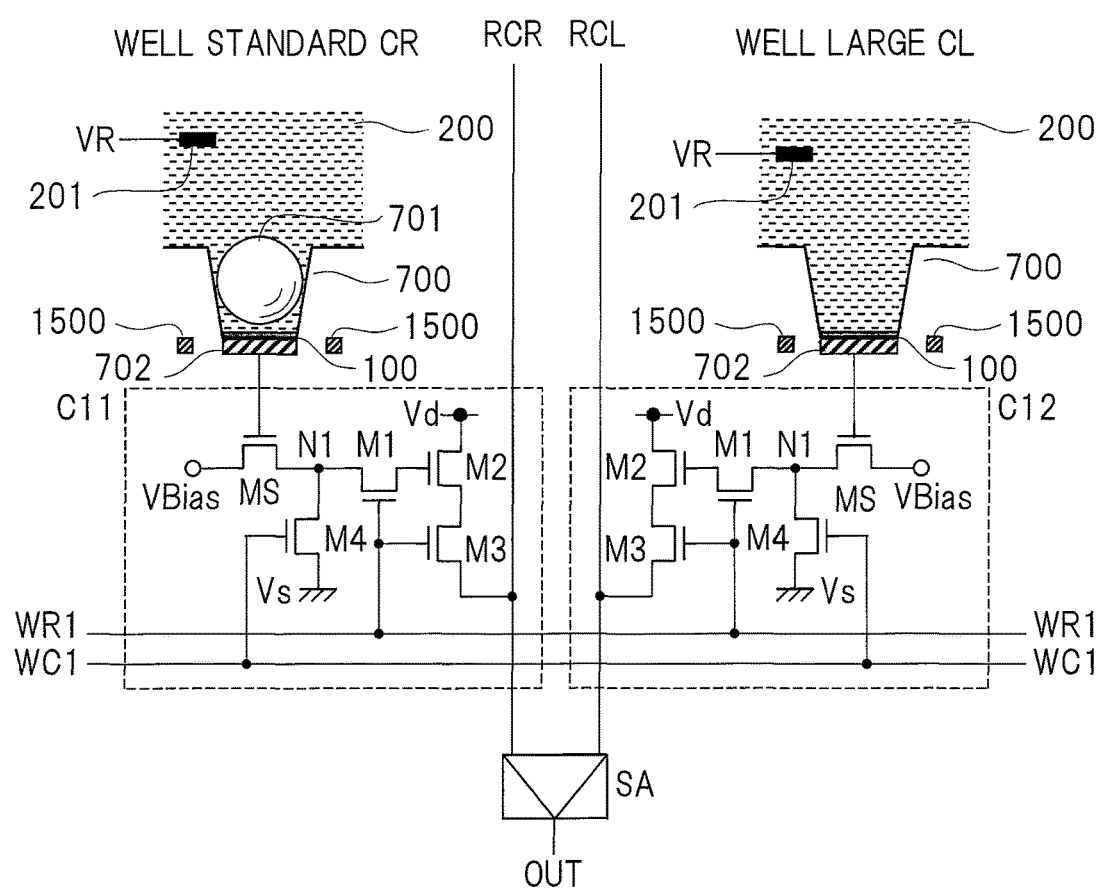
Figure 23:
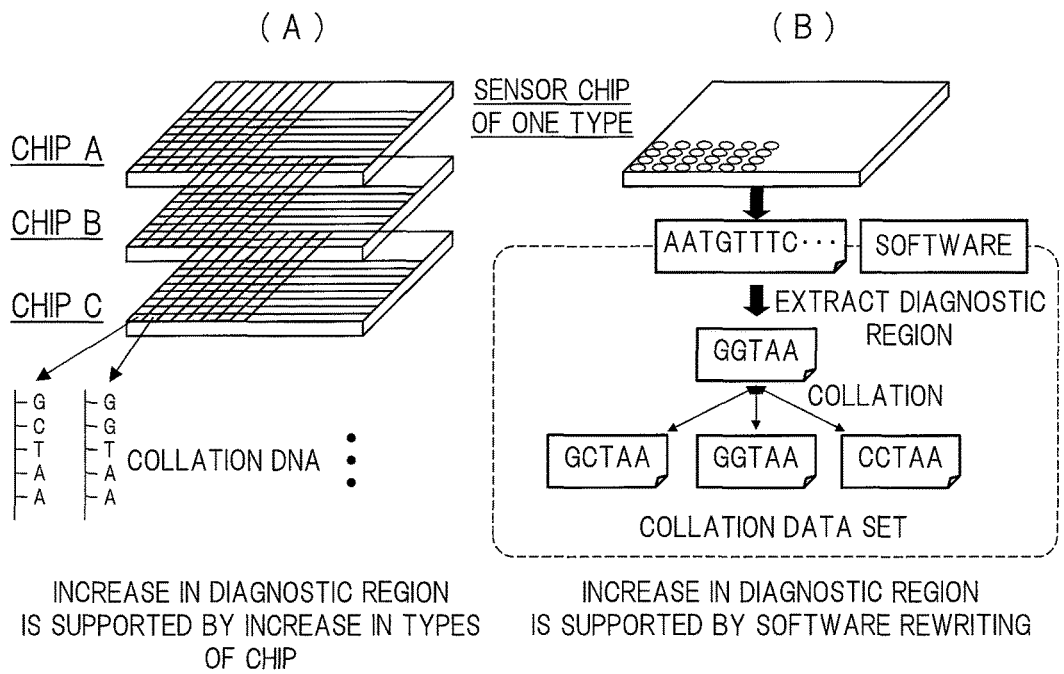
Figure 24:
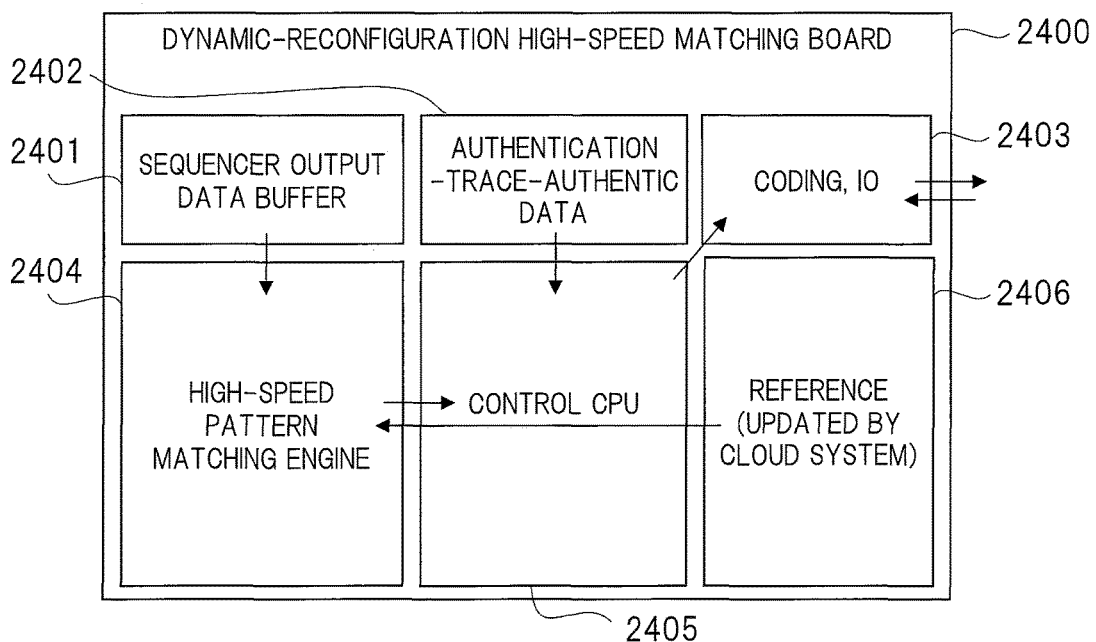

FIG. 17(A) and FIG. 17(B) are waveform diagrams for explaining operations of a biomolecule measuring device;

FIG. 18 is a waveform diagram for explains an operation of the biomolecule measuring device;

FIG. 19 is a circuit diagram showing a configuration of a cell according to a sixth embodiment;

FIG. 20 is a circuit diagram showing a configuration of a cell;

FIG. 21 is a waveform diagram for explaining an operation of the biomolecule measuring device;

FIG. 22 is a circuit diagram showing a configuration of a semiconductor sensor according to a seventh embodiment;

FIG. 23(A) and FIG. 23(B) are diagrams showing functions of a data processing unit of the biomolecule measuring device; and FIG. 24 is a diagram showing the configuration of the data processing unit of the biomolecule measuring device.

DETAILED DESCRIPTION OF PREFERRED EMBODIMENTS

Hereinafter, embodiments of the present invention will be described in detail with reference to the accompanying drawings. Note that the same components are denoted by the same reference symbols in principle throughout all the drawings for describing the embodiments, and the repetitive description thereof will be omitted.

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof. Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specified number is also applicable. Further, in the embodiments described below, it goes without saying that the components (including element steps) are not always indispensable unless otherwise stated or except the case where the components are apparently indispensable in principle.

Similarly, in the embodiments described below, when the shape of the components, positional relation thereof, and the like are described, the substantially approximate and similar shapes and the like are included therein unless otherwise stated or except the case where it is conceivable that they are apparently excluded in principle. The same goes for the numerical value and the range described above.

First Embodiment

A semiconductor sensor is manufactured on one semiconductor substrate by using a semiconductor technique. That is, the semiconductor sensor is formed on one semiconductor substrate by using the semiconductor technique so as to have a plurality of cells that are arranged in an array form on the semiconductor substrate. In the biomolecule measuring device, for example, the semiconductor sensor is set as explained later with reference to FIG. 6.

In the present embodiment, each of the plurality of cells arranged in the array form is provided with an ISFET and with a transistor having an amplifying function in order to increase the sensitivity, and besides, is provided with a transistor capable of performing an operation for reducing an offset of the ISFET and with signal wires required for this operation. While a plurality of embodiments will be explained below, an N channel-type field effect transistor (MOSFET) formed on a semiconductor substrate is assumed to be used as the transistor in the following explanations. Of course, the N channel-type MOSFET field effect transistor is merely one example, and various transistors can be used.

Figure 1:
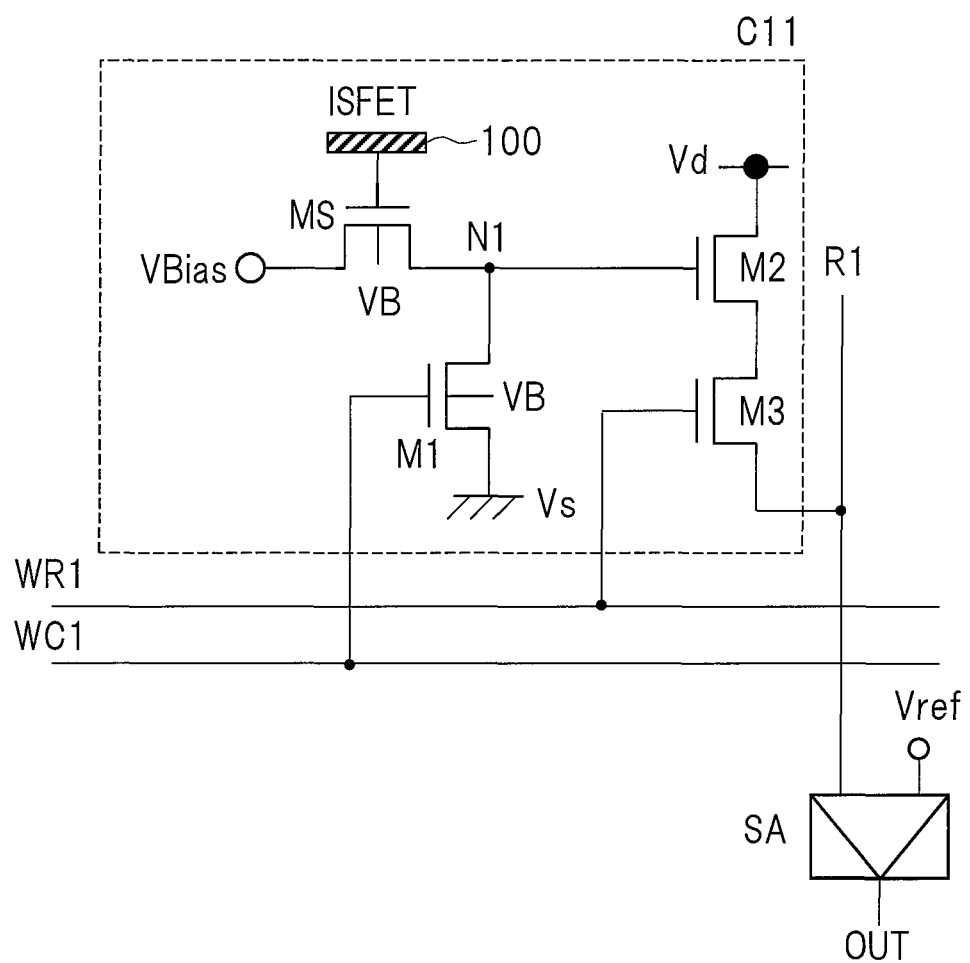

FIG. 1 is a circuit diagram showing a configuration of a cell according to the present embodiment. In this drawing, a configuration of one cell C11 of the plurality of cells arranged in the array form is shown. The plurality of cells arranged in the array form have mutually the same configuration as each other.

In FIG. 1, each of reference numerals M1 to M3 indicates a MOSFET. The cell C11 includes an ISFET, a first MOSFET M2, a second MOSFET M3 and a third MOSFET M1. The ISFET has an MOSFET MS having a floating gate and an ion sensitive layer 100. In the device configuration of the ISFET, an ion sensitive layer 100 of the ISFET is immersed in a solution although one explain is explained with reference to FIG. 2(A) and FIG. 2(B) later. Moreover, the MOSFET MS formed on the ISFET functions as a MOSFET having a floating gate.

To the drain electrode (terminal) of the MOSFET MS, a voltage in accordance with an operation is applied as a bias voltage "VBias", and the source electrode (terminal) of the MOSFET MS is connected to a node N1. To the back gate (in this example, semiconductor substrate) of the MOSFET MS, a control voltage "VB" is applied as a back bias voltage. This control voltage VB may be applied independently from the back bias voltage applied to the back gate of the other MOSFETs M1 to M3 within the cell C11, or may be commonly applied. FIG. 1 shows an example in which the control voltage VB is also applied to the back gate of the MOSFET M1. When it is independently applied, note that a semiconductor region having a different electric polarity is provided and formed for electrical insulation from the other MOSFETs as well known in the semiconductor technique.

The node N1 to which the source electrode of the MOSFET MS is connected is connected with the MOSFETs M1 and M2. This configuration is one of features of the present embodiment. That is, the source electrode (node N1) of the MOSFET MS inside the ISFET is connected to the drain electrode of a third MOSFET M1. Moreover, the gate of the third MOSFET M1 is connected to an offset cancel signal wire WC1, and is driven by the offset cancel signal wire WC1. By using this configuration, the offset of the MOSFET MS inside the ISFET can be reduced as described later. Here, the offset of the MOSFET MS inside the ISFET, in other words, the offset of the ISFET, is caused by, for example, a charge accumulated at the time of its manufacturing process. Since the quantity of charge to be accumulated is different depending on a position of the semiconductor substrate, the threshold voltage of the MOSFET MS appears as a value that is different for each of cells arranged in the array form.

In the present embodiment, by adjusting this, the threshold voltages of the respective MOSFETs MS (ISFET) can be made close to the same value as each other. That is, for each of the cells, a different change amount can be provided to the threshold voltage. Moreover, the control voltage VB to be applied to the back gate of the MOSFET MS inside the ISFET is set to a predetermined value, and a negative voltage is applied to the solution in which the ion sensitive layer 100 is immersed as a control voltage VR, so that the offset can be directed toward a direction reversed to the changing direction of the threshold voltage to be applied to the MOSFET MS by using the MOSFET M1.

As a further feature of the present embodiment, the source electrode (node N1) of the MOSFET MS is also connected to the gate of the first MOSFET M2. A gate of one electrode (source electrode or drain electrode) of the MOSFET M2 is connected to a readout signal wire WR1, and is connected to a readout wire R1 through a second MOSFET M3 controlled by the readout signal wire WR1. By this configuration, a signal change detected by the ion sensitive layer 100 connected to the MOSFET MS is amplified by the MOSFET M2 through the MOSFET MS. The amplified signal is selectively transmitted to a readout wire by the MOSFET M3. In this selective transmitting operation, the MOSFET M3 is controlled independently from the MOSFET M1 by the readout signal wire WR1. That is, the operation for changing the threshold voltage of the MOSFET MS (ISFET) by the MOSFET M1 and the transmitting operation described above can be controlled independently from each other. This point is also one of features of the present embodiment. By this feature, after the threshold voltage of the MOSFET MS is set to a predetermined value, a signal from the MOSFET MS can be amplified and outputted. Thus, the increase in the sensitivity can be achieved.

For example, in the technique shown in Patent Document 2, a signal from the MOSFET MS can be amplified. However, since the signal of the MOSFET MS itself has an offset, it becomes difficult to take out the signal detected by the ion sensitive layer with high sensitivity. The readout wire R1 is connected to one of inputs of a sense amplifier SA. The sense amplifier SA amplifies a voltage difference between a reference voltage "Vref" applied to the other input and the readout wire R1 connected to one input, and outputs its result to an "OUT".

As can be understood from FIG. 1, note that the other electrode (drain electrode or source electrode) of the MOSFET M2 is connected to a power supply voltage Vd, and one electrode (source electrode or drain electrode) of the MOSFET M2 is connected to the other electrode (drain electrode or source electrode) of the MOSFET M3. Moreover, one electrode (source electrode or drain electrode) of the MOSFET M3 is connected to the corresponding readout wire R1. In other words, the MOSFET M2 and MOSFET M3 are connected in series to each other between the power supply voltage Vd and the readout wire R1.

Furthermore, the other electrode (drain electrode or source electrode) of the MOSFET M1 is connected to the source electrode (node N1) of the MOSFET MS, and one electrode (source electrode or drain electrode) of the MOSFET M1 is connected to a circuit ground voltage "Vs". In other words, the MOSFET MS (ISFET) and the MOSFET M1 are connected in series to each other between the bias voltage VBias and the circuit ground voltage Vs. Since the MOSFET M1 is connected in series to the MOSFET MS inside the ISFET, the source electrode (node N1) of the MOSFET MS becomes at the circuit ground voltage Vs when the MOSFET M1 is turned on. Thus, the MOSFET MS can form a channel for causing an electric current to flow between the bias voltage VBias and the node N1.

According to the present embodiment, the sensitivity of each cell including the ISFET and being arranged in the array form can be increased.

FIG. 2(A) and FIG. 2(B) are schematic views for explaining a scheme for cancelling an offset. That is, FIG. 2(A) and FIG. 2(B) show change of the threshold voltage of the MOSFET MS by using the MOSFET MS, the MOSFET M1 and signal wires required for operating them. FIG. 2(A) and FIG. 2(B) show schematic cross-sectional views of the MOSFET MS and the MOSFET M1 of elements forming the cell C11 shown in FIG. 1. In FIG. 2(A) and FIG. 2(B), the shown structures of the MOSFET MS and the MOSFET M1 are the same as each other.

In FIG. 2(A), the ISFET has the MOSFET MS and the ion sensitive layer 100 connected thereto. In this embodiment, the sensitive layer 100 is connected to a floating gate 203 of the MOSFET MS through an insulating film 209. In FIG. 2(A), a reference numeral 200 represents a flow cell set on the semiconductor sensor. The flow cell 200 is filled with a solution 201. The solution 201 is, for example, a mixed solution between a biomolecular sample and a reagent. Moreover, a reference electrode 202 is provided in the flow cell 200, and a reference-use control voltage "VR" is applied to the reference electrode 202.

In this drawing, the ion sensitive layer 100 portion of the ISFET is immersed into the solution 201 shown on the upper side, and the MOSFET MS having the floating electrode 203 as its gate electrode is formed through the insulating film 209. The MOSFET MS has a semiconductor region 205 forming a source region corresponding to one electrode and a semiconductor region 204 forming a drain region corresponding to the other electrode, and these semiconductor regions 204 and 205 are formed on the semiconductor substrate 208. Moreover, the gate electrode of the MOSFET MS is arranged in a portion which is on the upper side of the semiconductor substrate 208 and which is between the above-described semiconductor regions 204 and 205.

The MOSFET M1 is arranged so as to be connected in series to the MOSFET MS. In the MOSFET M1 in the present embodiment, the semiconductor region 205 formed on the semiconductor substrate 208 is set to a semiconductor region (drain region) corresponding to the other electrode, and the semiconductor region 206 formed on the semiconductor substrate 208 is similarly set to a semiconductor region (source region) corresponding to one electrode. Moreover, the MOSFET M1 has a gate electrode in a portion which is on the upper side of the semiconductor substrate 208 and which is between the semiconductor regions 205 and 206. Although not particularly limited, the above-described semiconductor region 205 functions as the source region of the MOSFET MS and the drain region of the MOSFET M1. In this manner, in the present embodiment, the semiconductor substrates 208 of the MOSFET MS and M1 are common, and the semiconductor substrate 208 also functions as back gates of the MOSFETs MS and M1, and the bias voltage VB is applied thereto. Note that the above-described MOSFETs M2 and M3 are also formed on the semiconductor substrate 208 as similar to the above-described MOSFET M1.

As described earlier, note that the present specification explains the case of the usage of N channel-type MOSFET as the MOSFET. Therefore, in FIG. 2(A), the semiconductor substrate 208 is a P-type semiconductor, and semiconductor regions 204 to 206 are N-type semiconductors. Moreover, the expression "source/drain" is changed depending on the electric potential. Therefore, in the present specification, it would be understood that the expression "source/drain" one example.

In this configuration, by using the combination of the control voltages VB and VR, two operations can be performed. In an operation shown in FIG. 2(A), for example, the circuit ground voltage Vs (0 V) is applied to the semiconductor substrate 208 as the control voltage VB. In this case, a negative voltage (for example, −5 V) is applied to the reference electrode 202 as the control voltage VR. At this time, for example, the circuit ground voltage Vs (0 V) is applied to the source (source electrode) and drain (drain electrode) of each of the MOSFETs MS and M1 as well as to the gate of the MOSFET M1. In this state, the solution 201 in the flow cell 200 becomes at a negative potential by the negative control voltage VR applied to the reference electrode 202. On the other hand, since the circuit ground voltage Vs is applied to the semiconductor substrate 208, the electric potential of the semiconductor substrate 208 becomes higher than the electric potential of the solution 201 in the flow cell 200. Thus, between the floating electrode 203 of the MOSFET MS and the semiconductor substrate 208, such a potential difference as to pull the negative charge accumulated in the floating gate 203 toward the semiconductor substrate 208 side is generated.

If the value of the control voltage VR to be applied to the reference electrode 202 is sufficiently large, for example, at −5 V, the negative charge accumulated in the floating electrode 203 is pulled out toward the semiconductor substrate 208 side. Although not shown in this drawing, an insulating film is placed between the floating electrode 203 and the semiconductor substrate 208. However, since an electron tunneling current flows, the negative charge is pulled out to the semiconductor substrate 208 as the tunneling current. Consequently, an operation for pulling out an excessive negative charge captured (accumulated) in the floating gate 203 can be performed because of the above-described reason.

In an operation shown in FIG. 2(B), the control voltage VB is set at, for example, the circuit ground voltage Vs (0 V), and the control voltage VR is set at, for example, a desired positive voltage. Moreover, for example, 5 V is applied to the drain of the MOSFET MS (at the bias voltage VBias of FIG. 1), and the same voltage (5 V) is also applied to the gate of the MOSFET M1. Furthermore, the source of the MOSFET M1 is set at, for example, the circuit ground voltage Vs (0 V). By setting the control voltage VR to a desired voltage, a current (ground current) is allowed to flow from the drain (drain region 204) of the MOSFET MS to the source (source region 206) of the MOSFET M1 through the commonly-used semiconductor region 205 in the MOSFETs MS and M1. At this time, a part of the ground current is injected to the floating electrode 203 as hot electrons. When the hot electrons are injected to the floating gate 203, the threshold voltage of the MOSFET MS is changed. In this manner, the operation shown in FIG. 2(B) is reversed to the operation shown in FIG. 2(A) in which the negative charge is pulled out, and the direction of the change in the threshold voltage can also be a direction reversed to the direction shown in FIG. 2(A).

In this manner, in the present embodiment, by using the MOSFETs MS, M1 and signal wires required for operating them, the threshold voltage of the MOSFET MS can be changed to a desired direction. That is, the offset of the MOSFET MS caused by the accumulation of charges can be cancelled.

FIG. 3(A) to FIG. 3(G) show operation waveform diagrams obtained when the operation shown in FIG. 2(B) is performed in the configuration of the cell C11 shown in FIG. 1. In this drawing, a horizontal axis represents the time. Moreover, in each of the waveforms, a vertical axis represents the voltage. In this explanation, as the solution 201 (shown in FIG. 2(B)), a solution having an appropriate pH is used for adjustment. Of course, a washing solution used for a practical measuring operation or a solvent for use in dissolving an enzyme may also be used.

According to the operation to be described below, a degree of the change in the threshold voltage of the MOSFET MS (ISFET) can be changed for each of the cells. In this manner, even when the MOSFET MS of the respective cells undesirably have different threshold voltages, that is, offsets, from each other due to, for example, the charge accumulation at the time of the manufacturing process, or become different from each other during a continuous operation, the threshold voltages can be unified to the same value as each other. Thus, a signal formed by a highly sensitive array can be obtained from the plurality of cells each of which includes the ISFET and has the amplifying function. Although explained while exemplified later, for example, a temperature of a reagent can be changed in a course of one measurement. By changing the threshold voltage prior to the change of the temperature, a signal obtained after the change of the temperature can be obtained with higher sensitivity.

Figure 2:
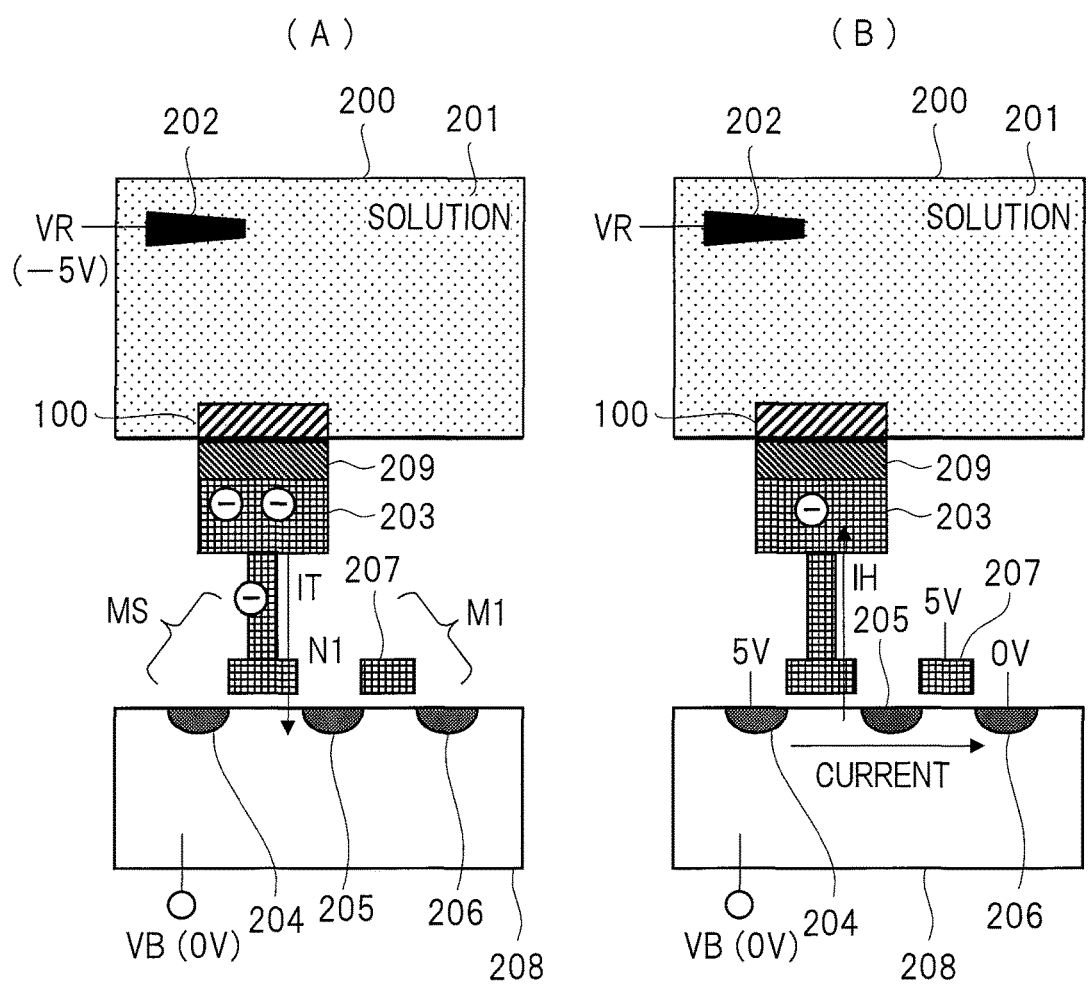
Figure 3:
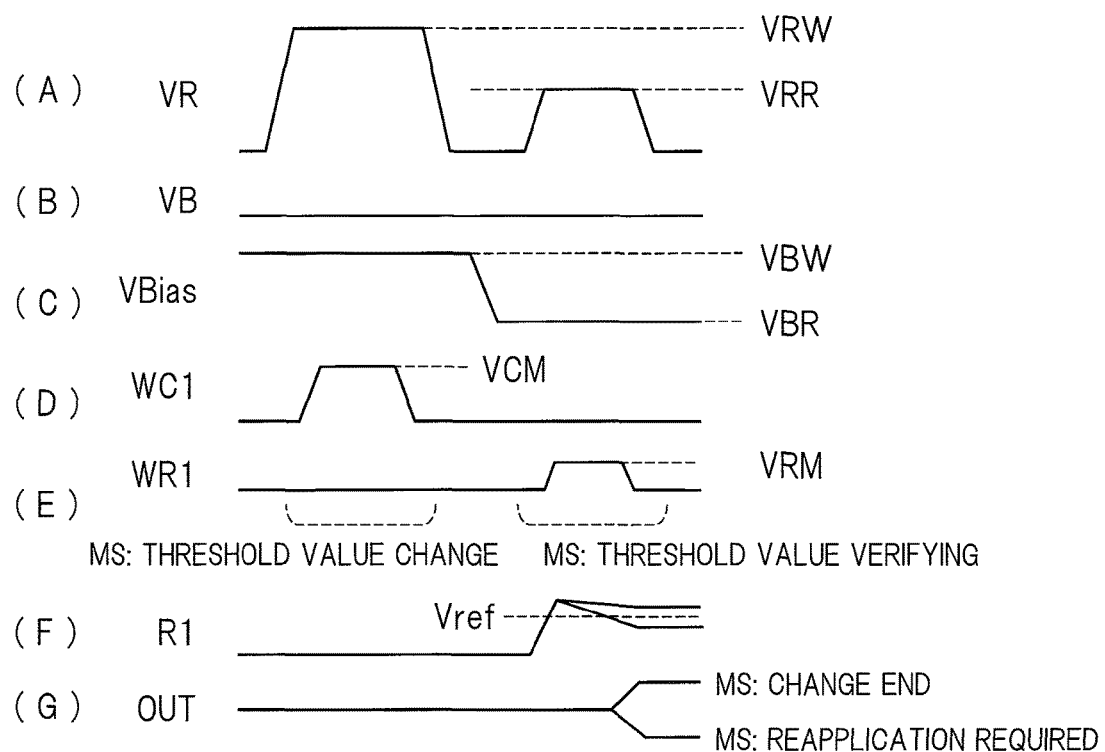

In FIG. 3, first, a desired signal voltage VRW is applied to the control voltage VR. That is, the value of the control voltage VR is set to "VRW". In this state, a signal voltage VCM (5 V in FIG. 2(B)) is applied to an offset cancel signal wire WC1 connected to the gate of the MOSFET M1. On the other hand, a voltage VBW (5 V in FIG. 2(B)) is applied to the bias voltage VBias. Thus, each of the MOSFETs MS and M1 is set to an ON state. In this state, as explained in FIG. 2(B), hot electrons are generated in the MOSFET MS, and some of the generated hot electrons are injected to the floating gate 203. Thus, during a period described as "MS: threshold value change" in FIG. 3, that is, during a period in which the offset cancel signal wire WC1 is set to a high level (VCM), the threshold voltage of the MOSFET MS can be changed.

Then, in the present embodiment, the signal of the ISFET (MOSFET MS) is readout. When the signal is read out, signal voltages VRR and VBR are applied to the control voltage VR and the bias voltage VBias, respectively. The respective voltage values of the signal voltages VRR and VBR are set to values lower than the above-described voltages VRW and VBW. Moreover, in order to perform the readout, the MOSFETs M2 and M3 are operated here. For this reason, a signal voltage VRM is applied to the readout signal wire WR1 for use in controlling the MOSFET M3. Thus, the signal corresponding to the state of the threshold value of the MOSFET MS at this time is read out (transmitted) onto the readout wire R1. The voltage of the readout wire R1 and a previously-determined reference voltage Vref are compared with each other by the sense amplifier SA, and it is determined whether or not the comparison result within a predetermined range, and the determination result is outputted to OUT. This process is referred to as a verifying operation in the present specification.

In the determination for the verifying operation, when it is determined that the comparison result is within the predetermined range, it is set that the threshold voltage of the MOSFET MS (ISFET) is within a predetermined range. On the other hand, it is determined that the comparison result is not within the predetermined range, it is set that the threshold voltage of the MOSFET MS (ISFET) is not within the predetermined range. Then, when the threshold voltage of the MOSFET MS (ISFET) is within the predetermined range, the operation for changing the threshold voltage of the MOSFET MS is not performed and ended. On the other hand, it is determined that the threshold voltage of the MOSFET MS is not within the predetermined range, the operation during the period "MS: threshold value change" shown in FIG. 3 is repeated.

With respect to each of the plurality of cells arranged in the array form, the operation of the threshold value change and the verifying operation for reading out the threshold value of the MOSFET MS (operation during "MS: threshold value verifying" period in FIG. 3) are alternately performed once or a plurality of times. In this case, in the "threshold value verifying" period, it is determined whether or not the operation of the threshold value change and the operation of the threshold value verifying are repeated in accordance with whether or not the threshold voltage of the ISFET is within the predetermined range. Thus, it is possible to sort the threshold voltages of the ISFET of the respective cells arranged in the array form can be almost equal to each other.

During the "MS: threshold value verifying" period in FIG. 3(D), note that the offset cancel signal wire WC1 is set to a low level. However, during this period, a predetermined signal voltage may be applied to the offset cancel signal wire WC1. In such a manner, a bias current is allowed to flow through the MOSFET M1 during this period so that an optimal voltage can be generated in the node N1 (FIG. 1). Moreover, as an example of the output OUT of the sense amplifier SA, FIG. 3(G) shows a case of the threshold voltage change of the MOSFET MS and a case of no change as "MS: re-application required" and "MS: change end".

FIG. 4(A) to 4(E) show waveform diagrams obtained when operations (first operation mode) explained in FIG. 2(A) is performed in the cell C11 shown in FIG. 1. In this operation mode, to the reference electrode 202, a control voltage VR having a signal voltage VRT serving as a negative voltage is applied as its voltage value. Thus, as explained in FIG. 2(A), a negative charge can be pulled out from the floating gate 203 to the semiconductor substrate 208. In FIG. 4(A), note that the control voltage VB to be applied to the semiconductor substrate 208 is set to a low level. However, as indicated by a one-dot chain line, the period of this operation may be set to a high level.

Figure 4:
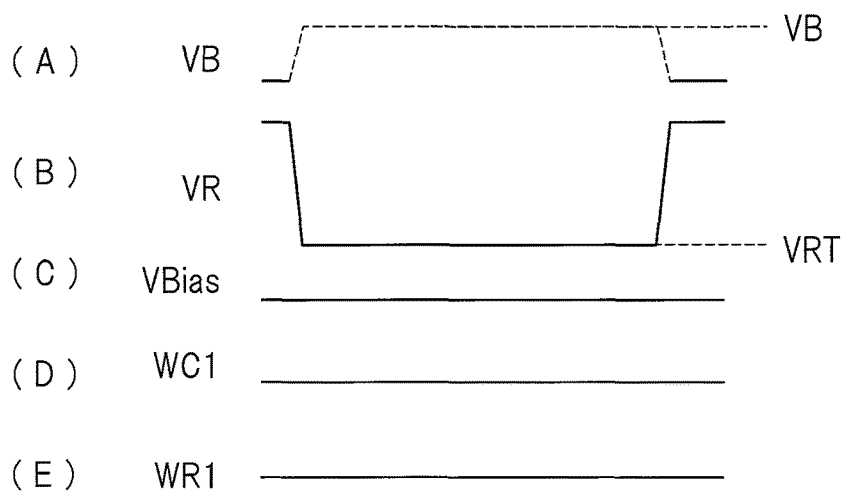

It is desired that, for example, the operation (FIG. 2(A)) shown in FIG. 4 is collectively performed to a plurality of cells arranged in the array form before the operation of FIG. 3 so as to largely move the threshold voltages of the MOSFET MS of all the cells toward one direction. By performing the operation shown in FIG. 3 after the operation shown in FIG. 4, the threshold voltages can be collectively moved, and then, the threshold value of each of the cells can be moved by a desired value in a direction reversed to this direction. Thus, even when the threshold voltages of the ISFET of the respective cells arranged in the array form are different from each other in a wide range, those values can be unified to almost the same value.

Note that each of the control voltage VB shown in FIG. 3(B) and the bias voltage VBias shown in FIG. 4 is set to, for example, the circuit ground voltage Vs.

Second Embodiment

Figure 5:
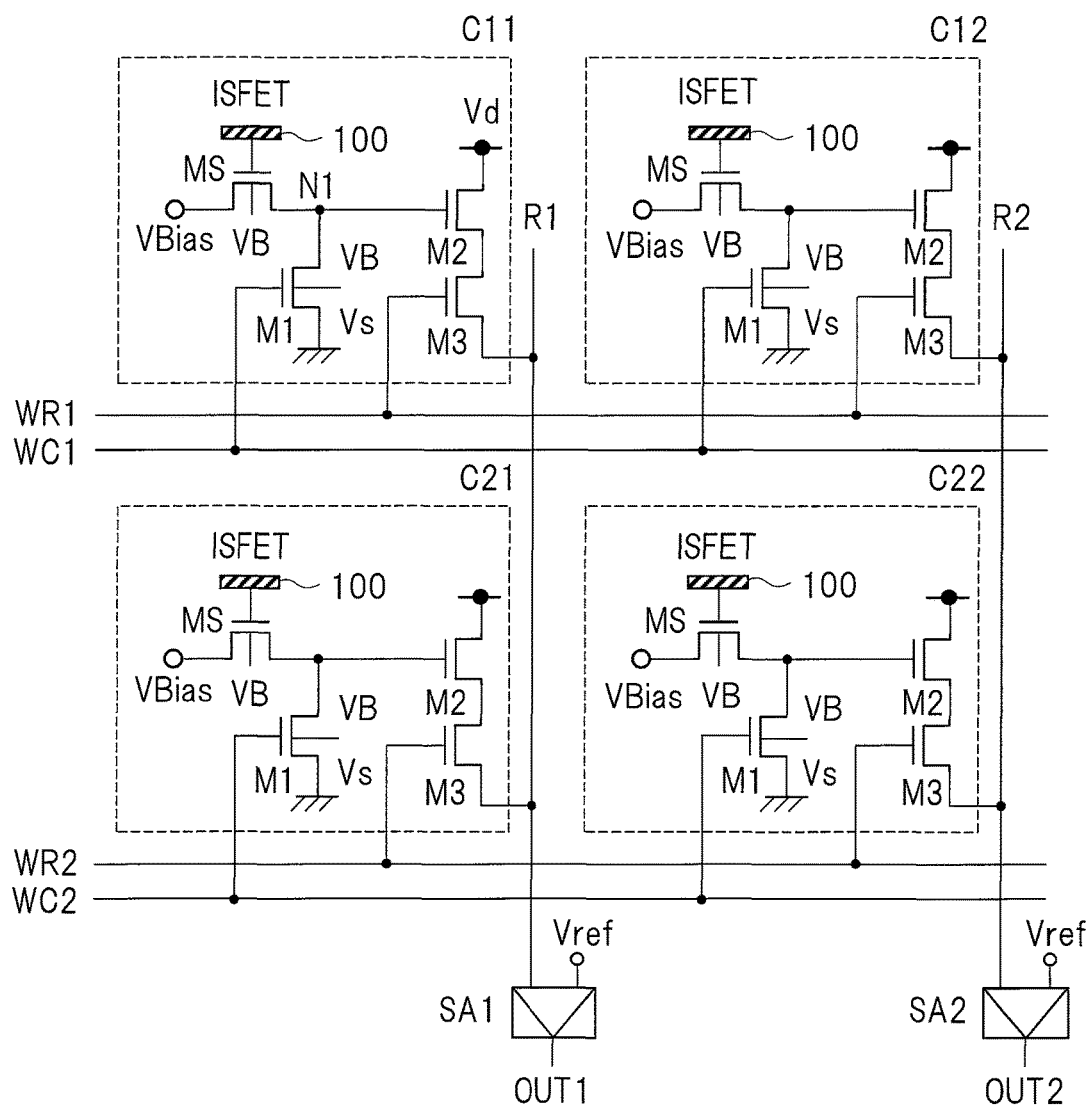
FIG. 5 is a circuit diagram showing a configuration of a semiconductor sensor according to a second embodiment.

FIG. 5 is a circuit diagram showing a configuration of a semiconductor sensor according to a second embodiment. This semiconductor sensor has a plurality of cells arranged in an array form. In FIG. 5, of the plurality of cells arranged in the array form, cells arranged in 2 rows and 2 columns are representatively shown. Moreover, in this drawing, signal wires WR1, WR2, WC1 and WC2, and readout wires R1 and R2, arranged on the array are also shown.

In this drawing, C11, C12, C21 and C22 are cells arranged in 2 rows and 2 columns in the array. The cells C11, C12, C21 and C22 have the same configuration as each other, and each configuration is the same as the configuration of the cell C11 explained in FIG. 1. On the array, the plurality of signal wires WR1, WR2, WC1 and WC2, as well as the readout wires R1 and R2 are arranged. In the plurality of cells arranged in the array form, to the plurality of cells C11 and C12 (C21 and C22) arranged on the same row, the readout signal wire WR1 and the offset cancel signal wire WC1 (WR2, WC2) corresponding to the row among the plurality of signal wires are connected. Moreover, in the plurality of cells arranged in the array form, to the plurality of cells C11 and C21 (C12 and C22) arranged on the same column, the readout wire R1 (R2) corresponding to the column among the plurality of readout wires is connected. Furthermore, to the respective readout wires R1 and R2, respective sense amplifiers SA1 and SA2 are connected. The connections among the respective cells, signal wires and readout wires are as similar to FIG. 1.

The operation for changing the threshold voltage value of the MOSFET MS in each of the cells C11, C12, C21 and C22 is the same as the operation previously explained with respect to FIG. 2 to FIG. 4.

In this embodiment, operations shown in FIG. 4 are collectively performed to the plurality of cells C11, C12, C21 and C22 forming the array. In this manner, the threshold voltages of the MOSFET MS in the respective cells are moved to one direction. Then, for example, the operation shown in FIG. 3 is performed for each of the rows of the array. That is, in FIG. 5, the operation shown in FIG. 3 is performed to each of the cells C11 and C12 (C21 and C22) arranged on the same row. In this manner, the threshold voltages of the cells are controlled so as to be set to a desired value in the unit of rows. In this case, also among the cells arranged on the same row, the charge quantities accumulated in the floating gate 203 of the MOSFET MS are considered to be different from each other. For this reason, also among the cells arranged on the same row, the number of repetitions in which the operation shown in FIG. 3 is performed changes in some cases. Moreover, since the sense amplifier SA is different for each of the columns, the operation shown in FIG. 3 can be performed in the unit of rows as described above, so that a speed of the operation for setting the threshold voltages within a predetermined range can be increased.

In this manner, even in a case of an array having an extremely large number of cells, the threshold voltages of the ISFET (MOSFET MS) of the respective cells can be unified to almost equal to each other, so that signals can be obtained at high sensitivity by the amplification-use MOSFET M2 provided in each of the cells.

For example, in the operation shown in FIG. 3, the threshold voltages of the MOSFET MS of the respective cells are set within a predetermined range, and then, biomolecules are measured. That is, the change in the hydrogen ion concentration caused by the elongation reaction of the DNA by the reagent is detected by using the plurality of cells arranged on the array. In this measurement, the outputs OUT1 and OUT2 of the sense amplifiers SA1 and SA2 form a signal indicating the change in the hydrogen ion concentration. Therefore, the changes in the hydrogen ion concentration among the plurality of cells (unit of rows) can be measured in parallel with each other. Of course, note that an operation for changing the threshold voltage may be performed in the middle of the measurement.

<Configuration of Biomolecule Measuring Device>

Figure 6:
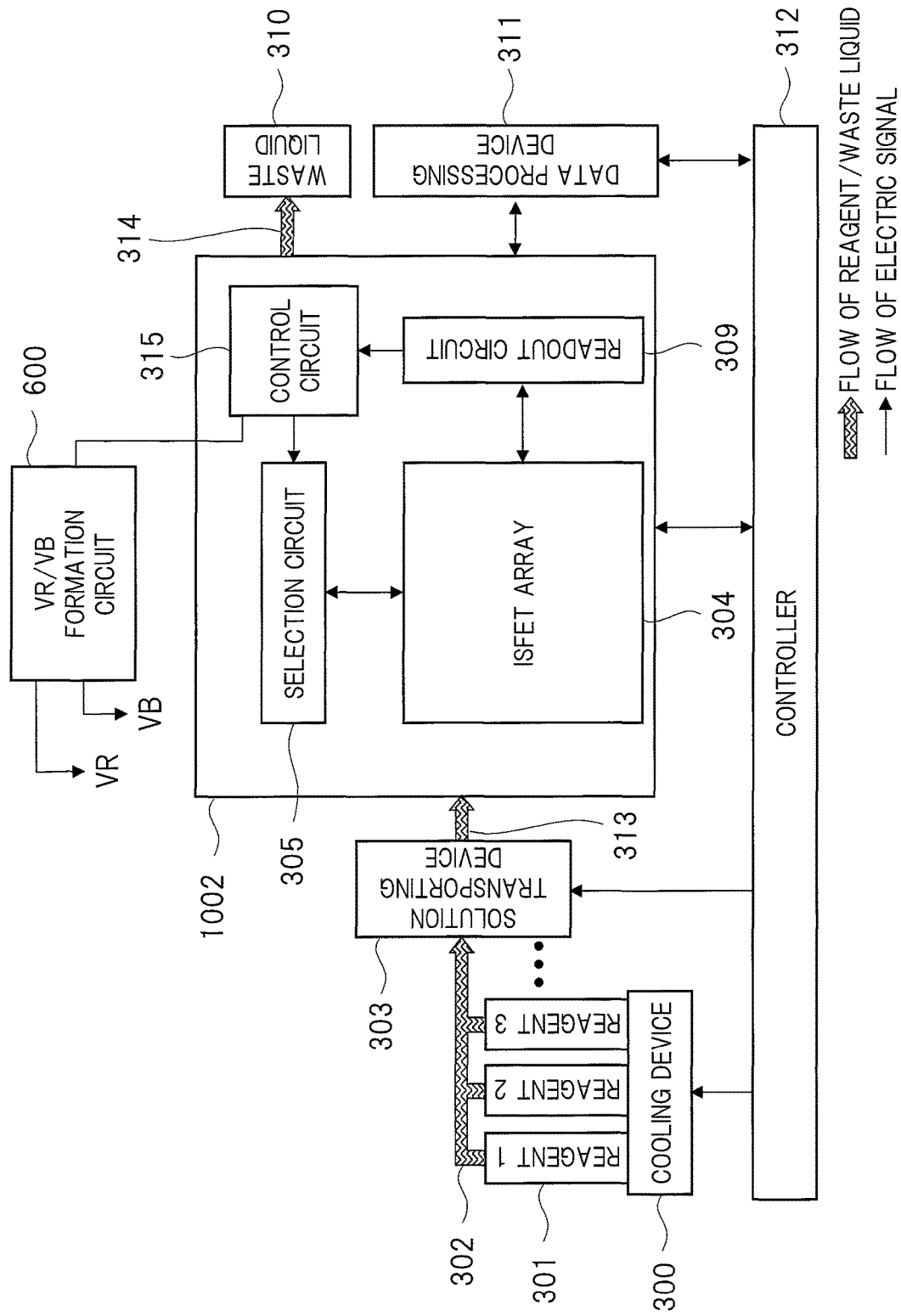
FIG. 6 is a block diagram showing a configuration of a biomolecule measuring device.

FIG. 6 is a block diagram showing an overall configuration of a biomolecule measuring device. A biomolecular sample to be measured is practically adhered to beads as described later, and is filled into a flow cell 200 (FIG. 2(A) and FIG. 2(B)) mounted on a semiconductor sensor (ISFET array chip) 1002.

The semiconductor sensor (ISFET array chip) 1002 is provided with an ISFET array 304, a selection circuit 305, a readout circuit 309 and a control circuit 315, and these devices are formed on one semiconductor substrate by using a semiconductor technique. The ISFET array 304 has the array described in FIG. 5. The selection circuit 305 controls the voltages of the readout signal wires WR1, WR2, and the offset cancel signal wires WC1, WC2 so as to select a plurality of cells from the ISFET array 304. For example, the readout signal wire WR1 is set to a high level, and the remaining readout signal wire WR2 is set to a low level, so that the plurality of cells C11 and C12 connected to this readout signal wire WR1 are selected. Signals from the selected cells are transmitted to the readout circuit 309 by the readout wires R1 and R2.

In order to perform operations explained with reference to FIG. 3 and FIG. 4, the control circuit 315 receives an output from the readout circuit 309, and controls the selection circuit 305 and a VR/VB formation circuit 600.

First, inn control of the operation shown in FIG. 4, in order to collectively change the threshold voltages of all the cells, such an instruction that all the readout signal wires WR1, WR2 and all the offset cancel signal wires WC1, WC2 are set to a low level is issued to the selection circuit 305. Moreover, at this time, the control circuit 315 causes the VR/VB formation circuit 600 for forming the control voltages VB and VR to form the voltages VR and VB shown in FIG. 4, so that the resulting voltages are applied to the reference electrode 202 provided on a follow cell 200 and the semiconductor substrate 208.

Furthermore, after the operation shown in FIG. 4 is executed, the control circuit 315 gives instructions to the selection circuit 305 so as to, for example, successively select the offset cancel signal wires WC1, WC2 in the ISFET array 304. At this time, the control circuit gives an instruction to the VR-VB formation circuit 600 so that the control voltages VB, VR and the bias voltage VBias as shown in FIG. 3 are formed so as to change the threshold voltage of the MOSFET MS in the selected cell, and are supplied to the reference electrode 202, the semiconductor substrate 208 and the respective cells. Note that, in order to avoid the complexed drawing, FIG. 6 does not show the bias voltage VBias supplied from the VR-VB formation circuit 600 to the ISFET array 304. However, in the present embodiment, the bias voltage VBias is also formed by the VR/VB formation circuit 600.

After the threshold voltage on the cell connected to the offset cancel signal wire WC1 is changed in the ISFET 304, the control circuit 315 executes the verifying operation (MS: threshold value verifying operation) explained in FIG. 3, and receives the result thereof from the readout circuit 309. In accordance with the received result, as explained in FIG. 3, for the cell whose threshold voltage is to be changed again, the selection circuit 305 and the VR/VB formation circuit 600 are controlled so that the operation for changing the threshold voltage is set while the offset cancel signal wire corresponding to the cell is set to a selection level. At this time, for the cell whose threshold voltage is not to be changed again, the operation of changing the threshold voltage is not performed. Moreover, when the result received from the readout circuit 309 indicates that no change of the threshold voltage is required for all the selected cells, a next offset cancel signal wire WC2 is selected as described above, and the same operation is repeated. In this manner, the threshold voltages of the MOSFET MS in all the cells included in the array are set to be within the predetermined range.

Now this description will return back to the explanation in the case of the measurement of the biomolecular sample. In the measurement of the biomolecular sample, one or a plurality of types of reagents are selected from a reagent container 301 by a solution feeding device 303, and is transported to the flow cell 200 through paths 302 and 313. The reagent transported to the flow cell 200 reacts with the biomolecular sample on the ISFET array chip 1002. The concentration change of ions that are products of this reaction is detected by the ISFET array 304. A waste liquid after the reaction is recovered by a waste liquid container 310 via a path 314. As a method of achieving the solution feeding device 303, for example, a plurality of general-use solution feeding pumps may be used, or an inert gas such as argon may be injected to the reagent container 301 while adjusting its pressure through a valve prepared for each of the reagent containers so that the reagent is pushed out from the container by gas pressure.

In accordance with a previously-programmed experiment sequence and data obtained by a data processing device 311, the controller 312 adjusts the solution feeding amount of the solution feeding pump of the solution feeding device 303, controls the operation state of the ISFET array chip 1002, also controls the data processing device 311 and further controls the voltage of the reference electrode (VR in FIG. 1) arranged on the reagent passage or the ISFET array. The data processing device 311 acquires and analyses the data outputted from the ISFET array chip 1002, and is configured by an interface board on which an A/D converter is mounted, and a calculation device (to be described later) and a computer for accelerating the processing.

In this drawing, the VR/VB formation circuit 600 is provided on the biomolecule measuring device separately from the semiconductor sensor. However, this circuit may also be formed on the same semiconductor substrate as that of the semiconductor sensor.

Figure 7:
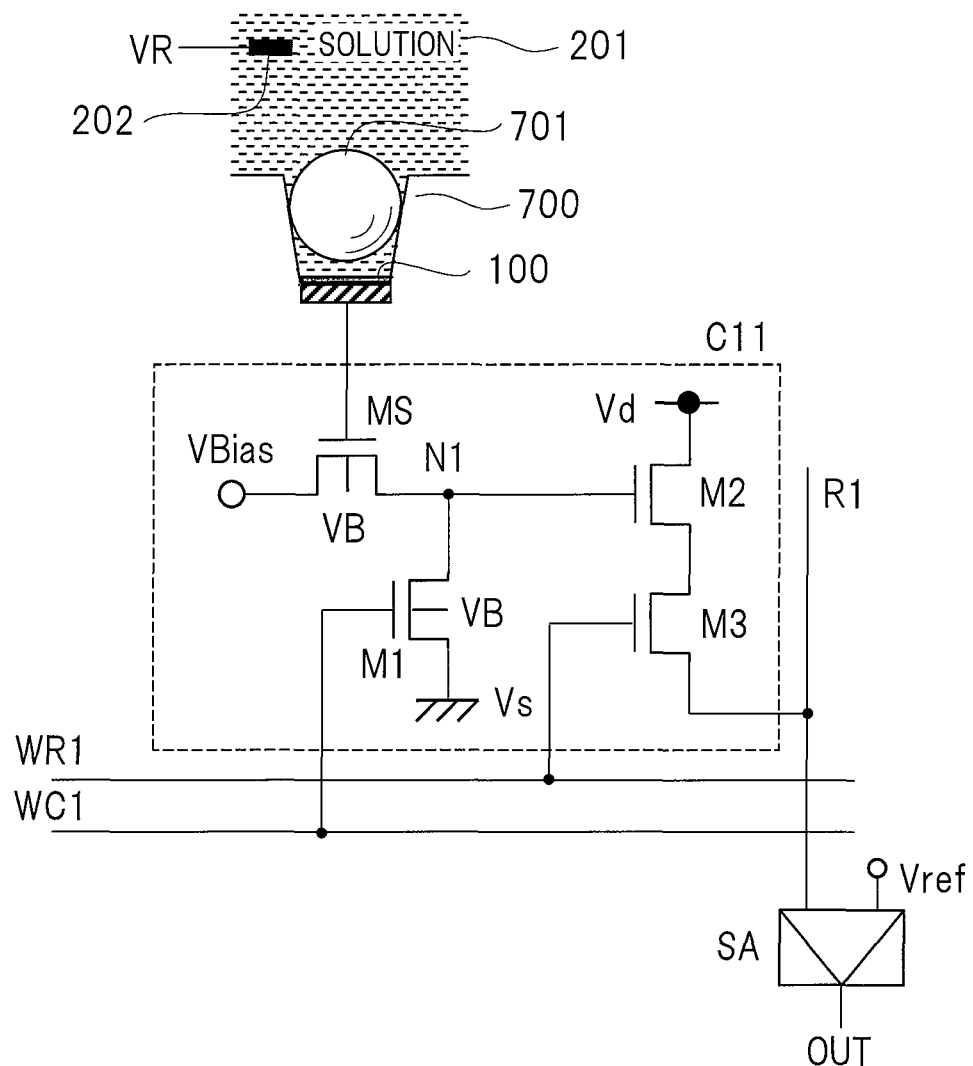
FIG. 7 is a schematic cross-sectional view of a semiconductor sensor.

FIG. 7 is a schematic cross-sectional view of the semiconductor sensor. In FIG. 7, C11 represents the cell shown in FIG. 1. In the semiconductor sensor, a well corresponding to each of the cells is provided on the upper side of the semiconductor substrate 208. In FIG. 7, the well corresponding to the cell C11 is denoted by a reference numeral 700. On the bottom surface of this well 700, an ion sensitive layer 100 of the ISFET inside the corresponding cell C11 is arranged. In the well 700, the solution 201 is made in contact with the ion sensitive layer 100. In this manner, the well 700 corresponds for each of the cells, and is such an independent reaction room as surrounding the sensitive layer 100 of the corresponding cell. To the well 700, beads 701 to which the measurement-target biomolecular sample is adhered are attached. As a material to be easily formed as a film in the semiconductor process among materials for the ion sensitive layer 100, silicon oxide $SiO_2$, silicon nitride $Si_3N_4$, aluminum oxide $Al_2O_3$, tantalum oxide $Ta_2O_5$, etc. are cited. These materials have different detection sensitivities from each other for each of the ions. For example, among the above-described materials, Ta$_2$O$_5$ has the highest detection sensitivity for hydrogen ions, while it has the lowest sensitivity for sodium ions. Therefore, Ta$_2$O$_5$ is preferably used for measuring hydrogen ions, in other words, for measuring a hydrogen-ion exponent pH of a solution.

<Configuration of Semiconductor Sensor>

Figure 8:
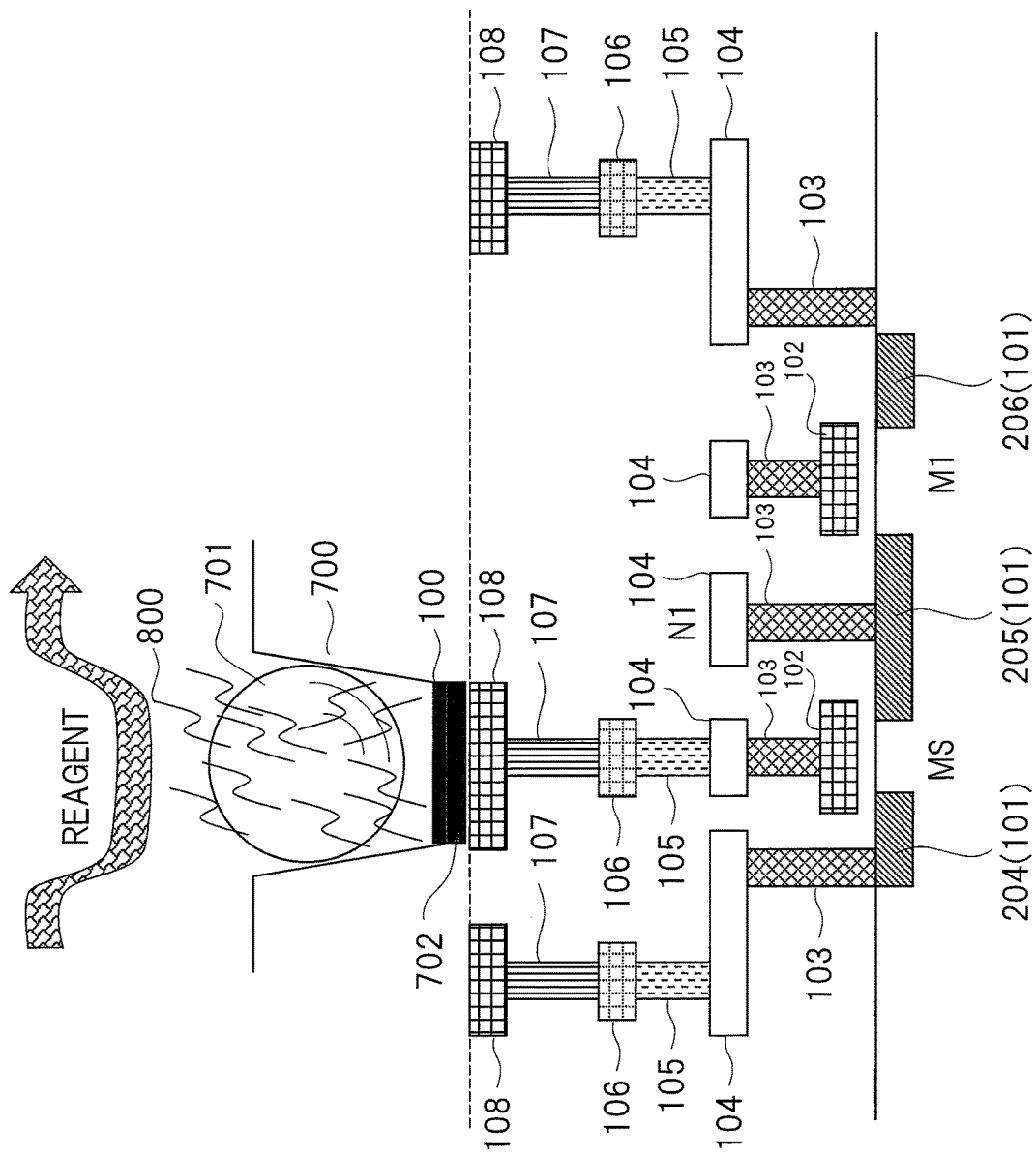
FIG. 8 is a cross-sectional view of a semiconductor sensor.

FIG. 8 shows a schematic cross-sectional view of a semiconductor sensor. This drawing also shows the cross sections of the MOSFETs MS and M1 included in the cell C11 together with the well 700. In FIG. 8, a reference numeral 101 represents a diffusion layer forming the source and the drain of the MOSFET, a reference numeral 204 (101) represents a drain diffusion layer of the MOSFET MS, and a reference numeral 206 (101) represents a source diffusion layer of the MOSFET M1. Moreover, a reference numeral 205 (101) represents a common diffusion layer between the MOSFETs MS and M1.

In FIG. 8, a reference numeral 102 represents a gate electrode of the MOSFETs MS and M1, and reference numerals 103, 105 and 107 represent metal layers for use in connecting metal wirings. Moreover, reference numerals 104, 106 and 108 represent metal wiring layers. The gate of the MOSFET MS reaches the upper portion through these metal layers so as to be connected to the ion sensitive layer 100 equivalently through the insulating layer. The metal layer becomes a floating gate. A shape of the well 700 that is the room in which the reaction occurs is formed by using the metal wiring in the upper layer. In the case of the DNA sequencer, beads 701 to which a large number of previously-grown DNA chains 800 of the same type are adhered are attached to the well 700. In this state, the reagent is flowed so that the change in the hydrogen ion concentration caused by the elongation reaction of DNA is measured.

The present embodiment has such features that the threshold voltages of the ISFET can be set to the same value among the wells 700, and that each cell has a function for amplifying the output of the ISFET. In this manner, the change in the hydrogen ion concentration can be detected with high sensitivity.

Figure 9:
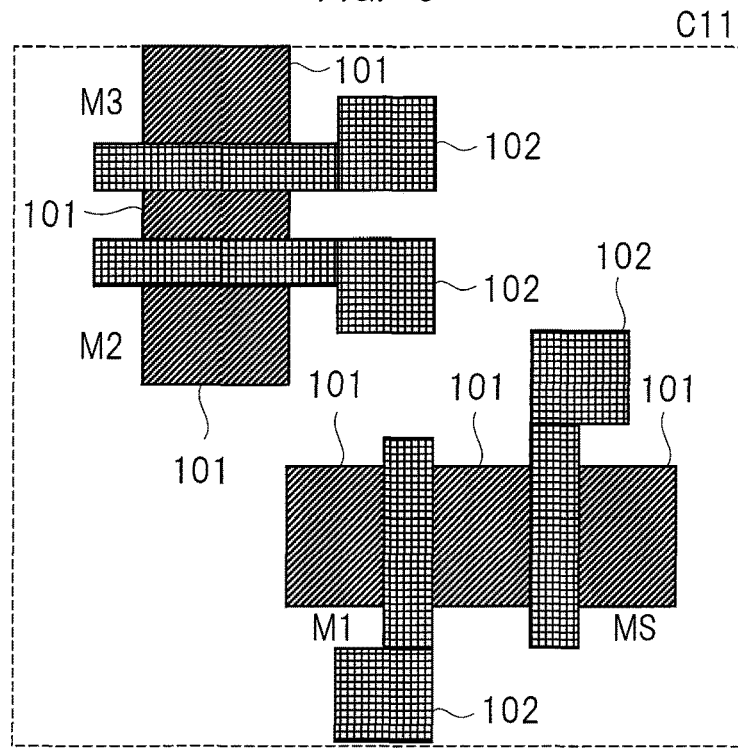
FIG. 9 is a plan view of a semiconductor sensor.
Figure 10:
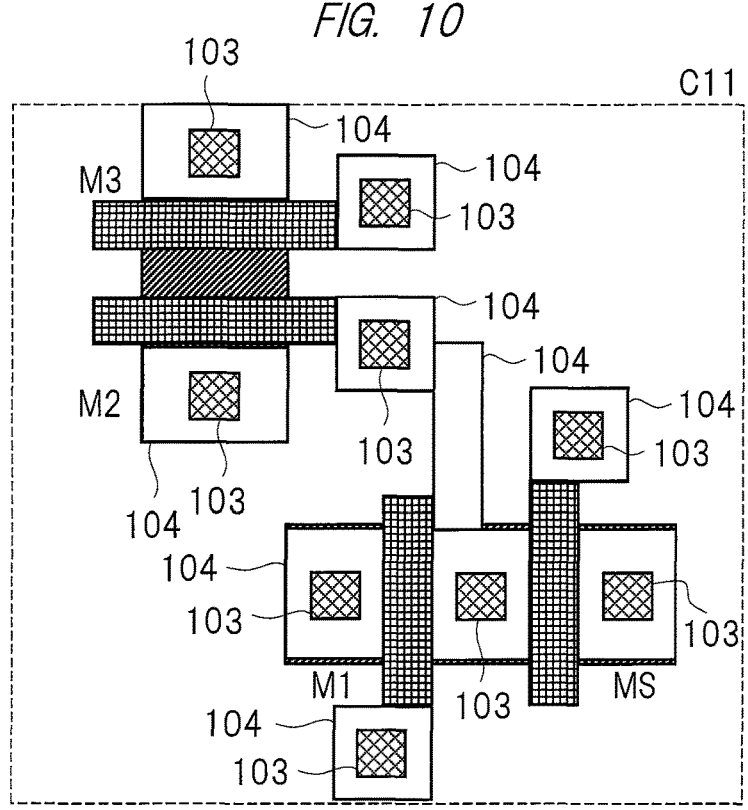
FIG. 10 is a plan view of a semiconductor sensor.
Figure 11:
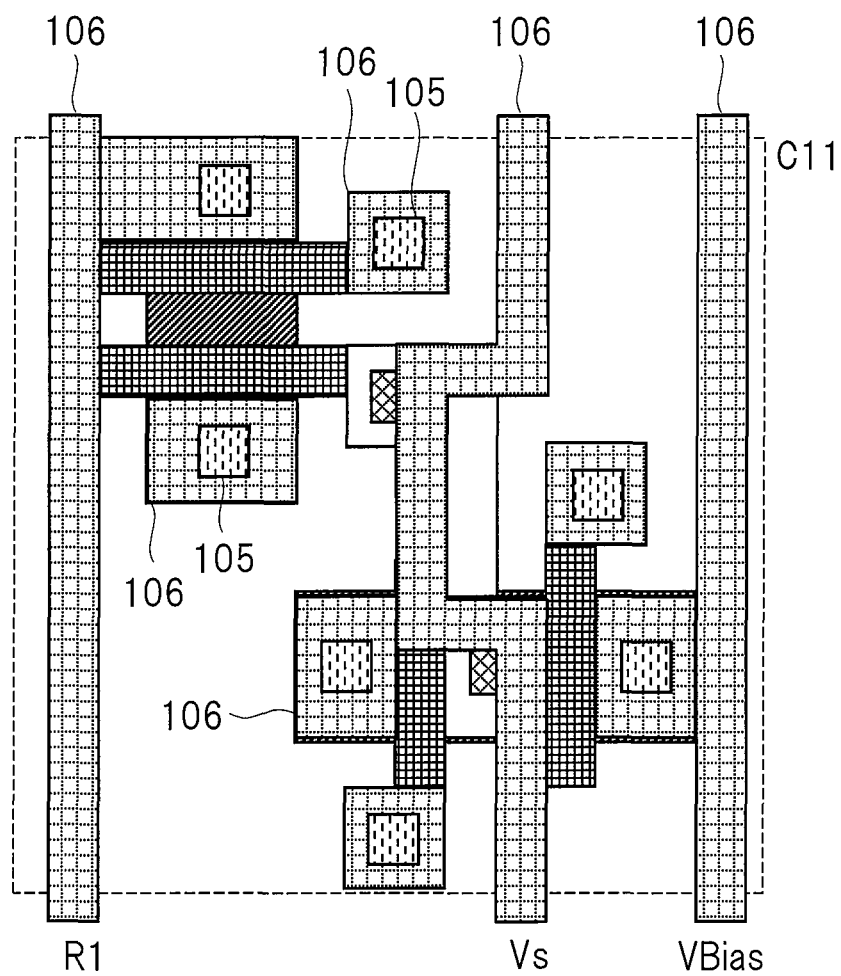
FIG. 11 is a plan view of a semiconductor sensor.

FIG. 9 to FIG. 11 are plan views showing the cell C11. On the semiconductor substrate 208, elements (MOSFET MS and MOSFETs M1 to M3) configuring the cell C11 are formed by using the semiconductor technique. FIG. 9 to FIG. 11 show planes (layout) in a manufacturing process for forming these elements by using the semiconductor technique. Note that the cross-sectional view shown in FIG. 8 and the plan views for each of the manufacturing processes shown in FIG. 9 to FIG. 11 are related to each other, and therefore, the manufacturing process of FIG. 9 to FIG. 11 will be described while also referring to FIG. 8.

In FIG. 9, a reference numeral 102 represents each of gate electrodes of the MOSFET MS, and M1 to M3, formed on a P-type semiconductor substrate 208 through an insulating layer. Moreover, a reference numeral 101 represents an N-type semiconductor region which is formed on the semiconductor substrate 208, and configures a source region and a drain region of each of these MOSFET. In FIG. 9 and FIG. 10, note that corresponding reference numerals MS and M1 to M3 are shown in regions corresponding to the MOSFET MS and M1 to M3, respectively. Although not particularly limited, the N-type semiconductor region 101 forming the source region and the drain region is formed to be self-aligned while the gate electrode is used as a mask. For example, by injecting ions to the P-type semiconductor substrate 208 while the gate electrode is used as a mask, the N-type semiconductor region 101 is formed. At this time, it is considered that charges accumulated since the gate electrode is also exposed to ions.

After forming the semiconductor regions corresponding to the gate electrode, the source region and the drain region, an interlayer insulating film is formed on the semiconductor substrate 208. A contact-use opening (hole) is formed in the formed interlayer insulating film, and a metal wiring layer 104 is formed on the interlayer insulating film. The metal wiring layer 104 is etched into such a shape as to form an electrode for an element. Moreover, a metal layer 103 is embedded into the opening opened from the interlayer insulating film. By the embedded metal layer 103, the metal layer 104 serving as the electrode of the element and the gate electrode of the element are connected to each other, and the metal wiring layer 104 serving as the electrode of the element and the source region as well as the drain region are connected to each other. FIG. 10 shows a state in which the electrode-use metal wiring 104 formed by the etching process is connected to the element as described above.

Furthermore, an interlayer insulating film is formed, and an opening is formed at a predetermined position of the interlayer insulating film. On the interlayer insulating film, a metal wiring layer 106 is formed, and is etched so as to have a predetermined plane shape. The metal wiring layer 106 formed as described above is electrically connected to the metal wiring layer 104 by the metal wiring layer 105 embedded in the opening. FIG. 11 shows the plane shape formed as described above. In FIG. 11, "R1" represents a readout wire, "Vs" represents a ground voltage wiring for supplying the circuit ground voltage, and "VBias" represents a voltage wiring for supplying a bias voltage VBias. In this embodiment, the readout wire R1, the ground voltage wire Vs and the voltage wire VBias are formed by the metal wiring layer 106.

Figure 12:
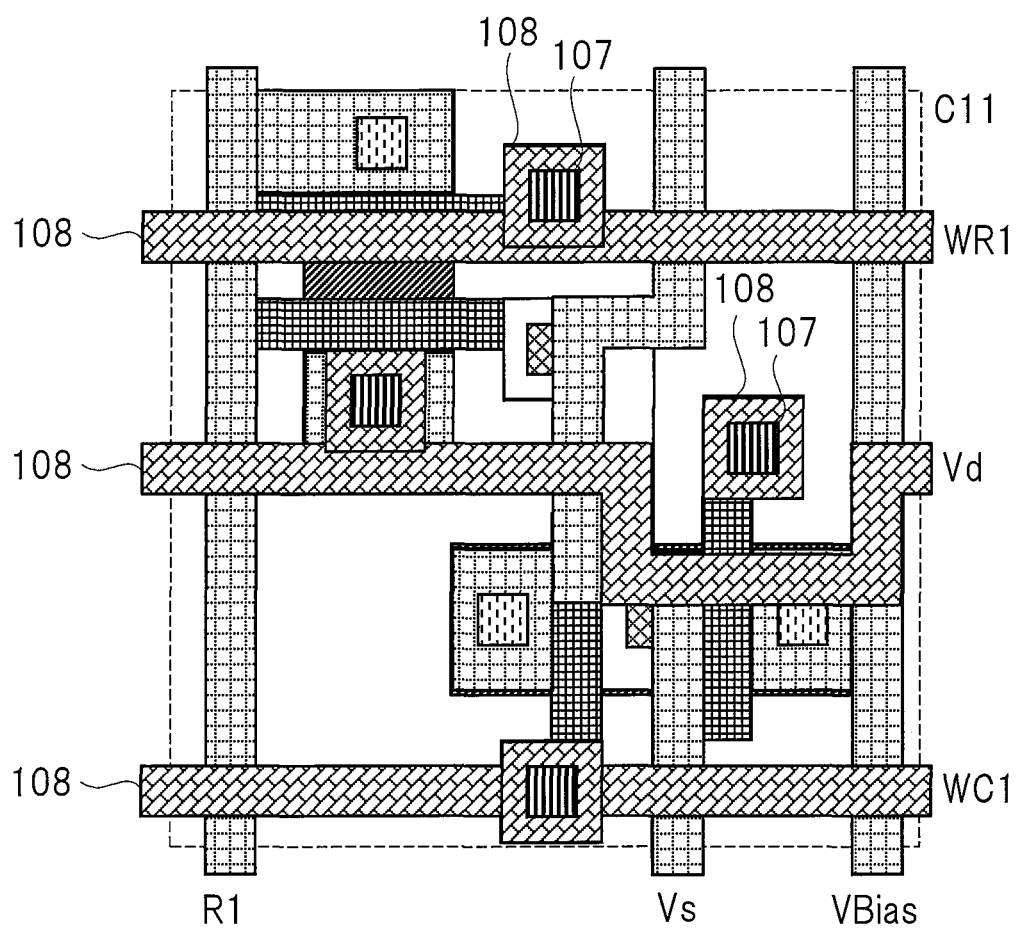
FIG. 12 is a plan view of a semiconductor sensor.

FIG. 12 shows a state in which the metal wiring 106 is formed, and then, the interlayer insulating film is formed, an opening is formed at a predetermined position of the interlayer insulating film, and a metal wiring layer 108 is further formed thereon. The metal wiring layer 108 is etched so as to have such a predetermined plane shape as to form a circuit. Moreover, the metal wiring layer 108 having the predetermined plane shape is electrically connected to the metal wiring layer 106 by a metal wiring layer 107 embedded into the opening. In FIG. 12, "WR1" and "WC1" represent signal wirings forming the readout signal wires WR1 and WC1 as explained earlier, and Vd represents a power-supply wire for supplying the power supply voltage Vd. In this embodiment, by the metal wiring layer 108 formed as an upper layer than the metal wiring layer 106, the signal wires WR1, WC1 and the power supply wire Vd are formed. Furthermore, in this embodiment, the signal wiring R1 that forms the readout wire R1 and the signal wires WR1 and WC1 are arranged (laid out) so as to be orthogonal to each other.

In the present embodiment, the floating gate of the MOSFET MS is formed by a plurality of stacked metal layers 102, 104 and 108, and by the metal layers 103, 105 and 107 for electrically connecting these metal layers. Although not shown in FIG. 12, an ion sensitive layer 100 is formed in an upper layer of the metal layer 108 forming the floating gate. The ion sensitive layer 100 is provided to the bottom surface of the well 700, and is surrounded by the well 700. By using this layout example, a cell having functions for changing the threshold voltages of the ISFET and for amplifying the output of the ISFET can be achieved.

Third Embodiment

Figure 13:
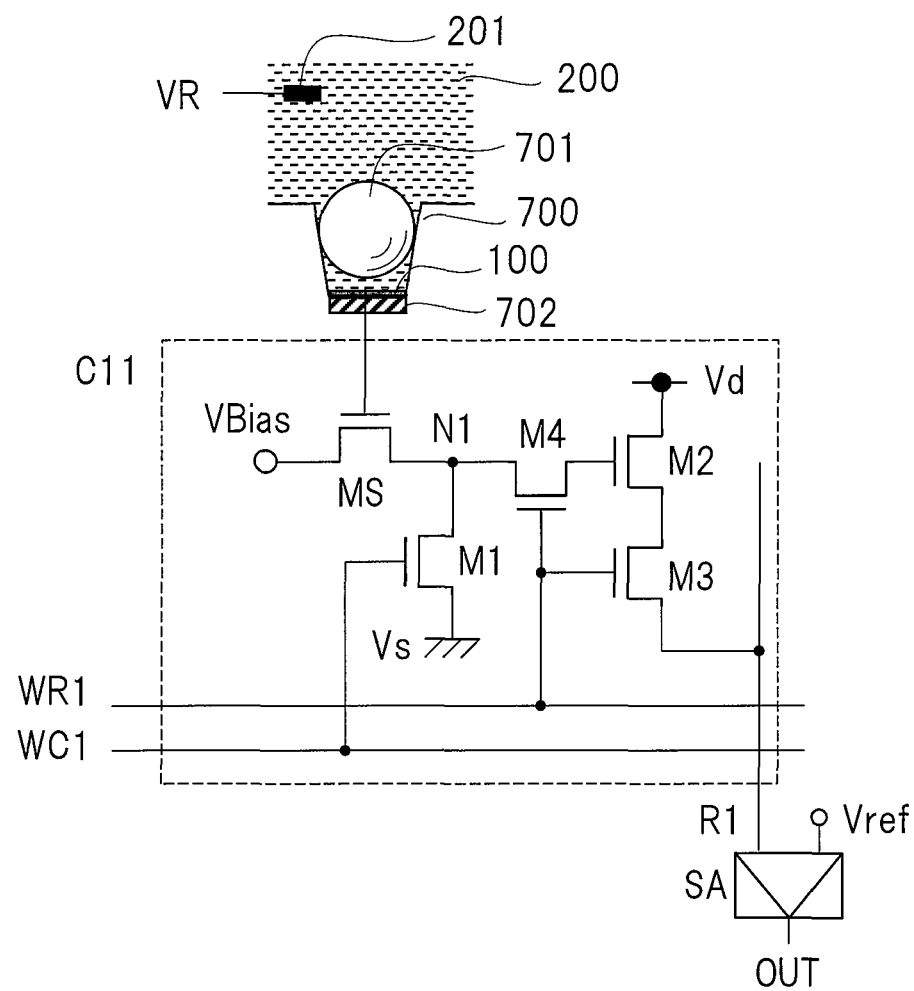
FIG. 13 is a circuit diagram of a semiconductor sensor according to a third embodiment.

FIG. 13 is a circuit diagram showing a configuration of a semiconductor sensor according to a third embodiment. The semiconductor sensor shown in FIG. 13 is similar to the semiconductor sensor shown in FIG. 7. Here, a part different from that of the semiconductor sensor shown in FIG. 7 will be mainly explained. From the semiconductor sensor shown in FIG. 7, the semiconductor sensor shown in FIG. 13 is different in the circuit configuration of the cell C11. In other words, the cell C11 shown in FIG. 13 is formed by adding an N-channel-type MOSFET M4 to the cell C11 shown in FIG. 7. The MOSFET M4 has a gate connected to the readout signal wire WR1 as similar to the gate of the MOSFET M3. Moreover, one of electrodes of the MOSFET M4 is connected to the gate of the MOSFET M2, and the other electrode thereof is connected to the node N1. Thus, the paired electrodes of the MOSFET M4 are electrically connected (turned on)/disconnected (turned off) in accordance with the value of the readout signal wire WR1. In other words, the MOSFET M4, which is turned on/off in accordance with the readout signal wire WR1, is connected in series between the node N1 and the gate of the MOSFET M3.

When the threshold voltage of the MOSFET MS is changed, the MOSFET M1 is turned ON by the voltage of the offset cancel signal wire WC1 as described earlier. On the other hand, at this time, the MOSFET M3 is turned OFF by the readout signal wire WR1. In this embodiment, when the threshold voltage of the MOSFET MS is changed, the MOSFET M4 is also turned OFF by the readout signal wire WR1. Thus, a high voltage (bias voltage VBias) for use in changing the threshold voltage of the MOSFET MS can be prevented from being applied to the gate of the MOSFET M2, so that the reliability of the cells can be improved. When the output of the MOSFET MS is read out, note that the readout signal wire WR1 is set to a high level, and the offset cancel signal wire WC1 is set to a low level, and therefore, the MOSFET M4 is turned ON, so that the output of the MOSFET MS is transmitted to the gate of the MOSFET M2 thorough the MOSFET M4. Although only one cell C11 is shown in FIG. 13 as a representative, cells shown in FIG. 13 are arranged in an array form as explained in FIG. 5 in the semiconductor sensor.

Fourth Embodiment

Figure 14:
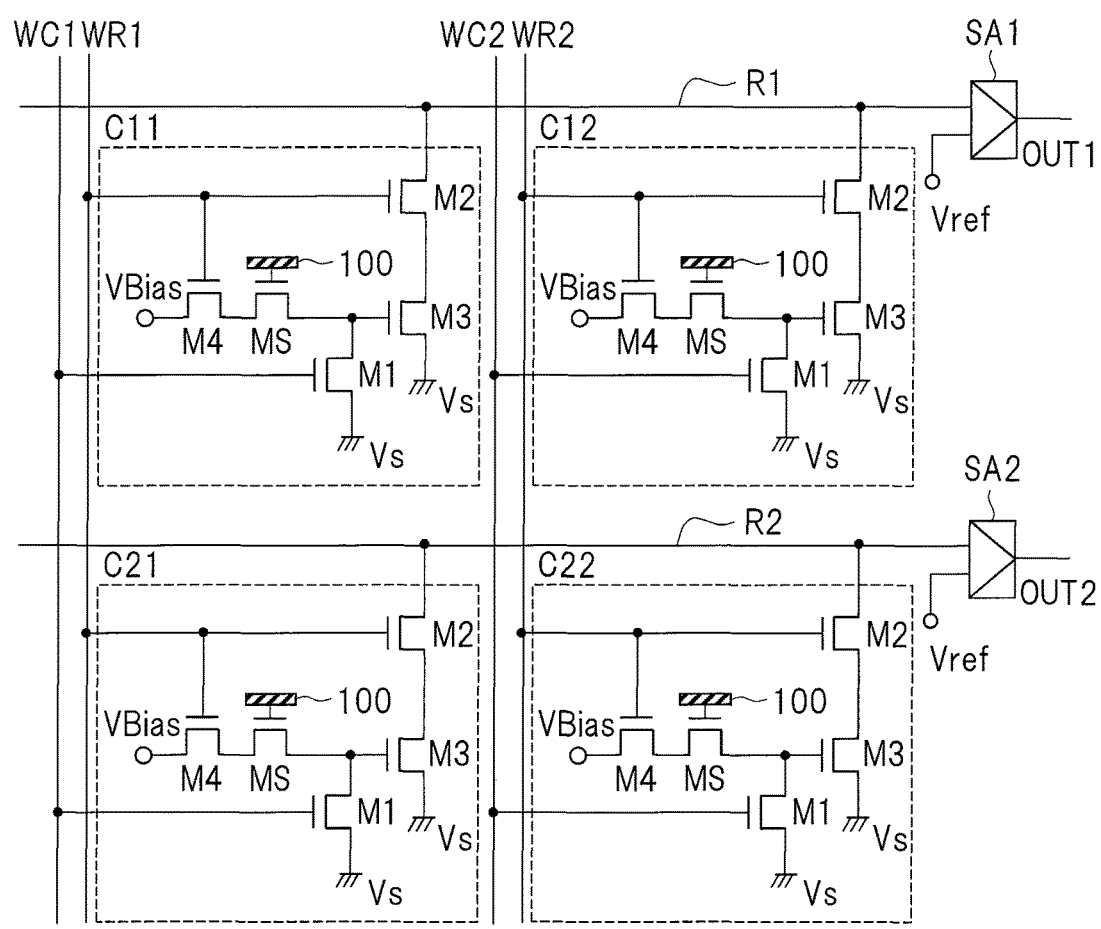
FIG. 14 is a circuit diagram of a circuit of a semiconductor sensor according to a fourth embodiment.

FIG. 14 is a circuit diagram showing a circuit configuration of a semiconductor sensor according to a fourth embodiment. This semiconductor sensor shown in FIG. 14 is similar to the semiconductor sensor shown in FIG. 5. In FIG. 14, a part different from that of FIG. 5 will be mainly explained. From the semiconductor sensor shown in FIG. 5, this is different in the cell configuration. That is, between FIG. 14 and FIG. 5, the plurality of cells arranged in the array form are different. Each of the cells C11, C12, C21 and C22 shown in FIG. 14 has the same configuration as each other. Therefore, the cell C11 will be explained here as a representative.

In the cell C1, one electrode of the MOSFET M2 is connected to the corresponding readout wire, and the other electrode thereof is connected to one electrode of the MOSFET M3. The other electrode of the MOSFET M3 is connected to the circuit ground voltage Vs. Moreover, the gate of the MOSFET M2 is connected to the readout wire WR1, and the gate of the MOSFET M3 is connected to one electrode of each of the MOSFET MS and MOSFET M1. The other electrode of the MOSFET M1 is connected to the circuit ground voltage Vs, and the other electrode of the MOSFET MS is connected to one electrode of the MOSFET M4, and the other electrode of the MOSFET M4 is connected to the bias voltage VBias. Moreover, the gate of the MOSFET M4 is connected to the readout signal wire WR1, and the gate of the MOSFET M1 is connected to the offset cancel signal wire WC1.

In this embodiment, the function for amplifying the signal of the ISFET (MOSFET MS) is given not to the MOSFET M2 (example of FIG. 1 and FIG. 13) but to the MOSFET M3. In this manner, the type of the MOSFET can be set to the P-channel-type MOSFET, or the voltage conditions to be applied to the MOSFET can be changed (the bias state can be changed) even in the case of the N-channel-type MOSFET as described earlier in the examples, so that the higher sensitivity can be achieved in some cases.

Moreover, in this embodiment, by providing the MOSFET M4 between the bias voltage VBias and the MOSFET MS, for example, application of a voltage to a device other than a desired ISFET in the array structure of FIG. 5 in changing the threshold voltage of the MOSFET MS can be avoided. In other words, by setting the readout signal wire WR corresponding to a cell whose threshold voltage is desirably changed to a high level and by setting the remaining readout signal wires WR to a low level, the bias voltage VBias can be applied to the ISFET inside the desired cell. At this time, the application of the bias voltage to the ISFET in a cell other than the desired cell can be prevented, and therefore, the change in the threshold voltage in the undesired ISFET due to the voltage applied to a portion other than the desired ISFET can be reduced.

In this embodiment, in changing the threshold voltage of the MOSFET MS, the readout signal wire (for example, WR1) corresponding to a cell (for example, C11) including the MOSFET MS is set to a high level, and the remaining readout signal wire WR2 is set to a low level. Moreover, at this time, the offset cancel signal wire WC1 is set to a high level, and the offset cancel signal wire WC2 is set to a low level. In this manner, the threshold voltage is changed in, for example, the cells on one column. At this time, in the cells on the other column, the application of the bias voltage VBias to the MOSFET MS can be avoided. Moreover, in reading out a signal of the cell, the offset cancel signal wires WC1 and WC2 are set to the low level, the readout signal wire WR (for example, WR1) corresponding to the cell to be read out is set to the high level, and the remaining readout signal wire WR2 is set to the low level.

The MOSFET having the function as described in this embodiment may be independently or jointly added. For example, in the configuration of FIG. 1, the MOSFET M4 may be provided between the bias voltage VBias and the MOSFET MS. Moreover, in the configuration of FIG. 1, the functions of the MOSFETs M2 and M3 may be changed to each other. Furthermore, the N-channel-type MOSFET may be replaced by or mixed with a P-channel-type MOSFET.

Fifth Embodiment

Figure 15:
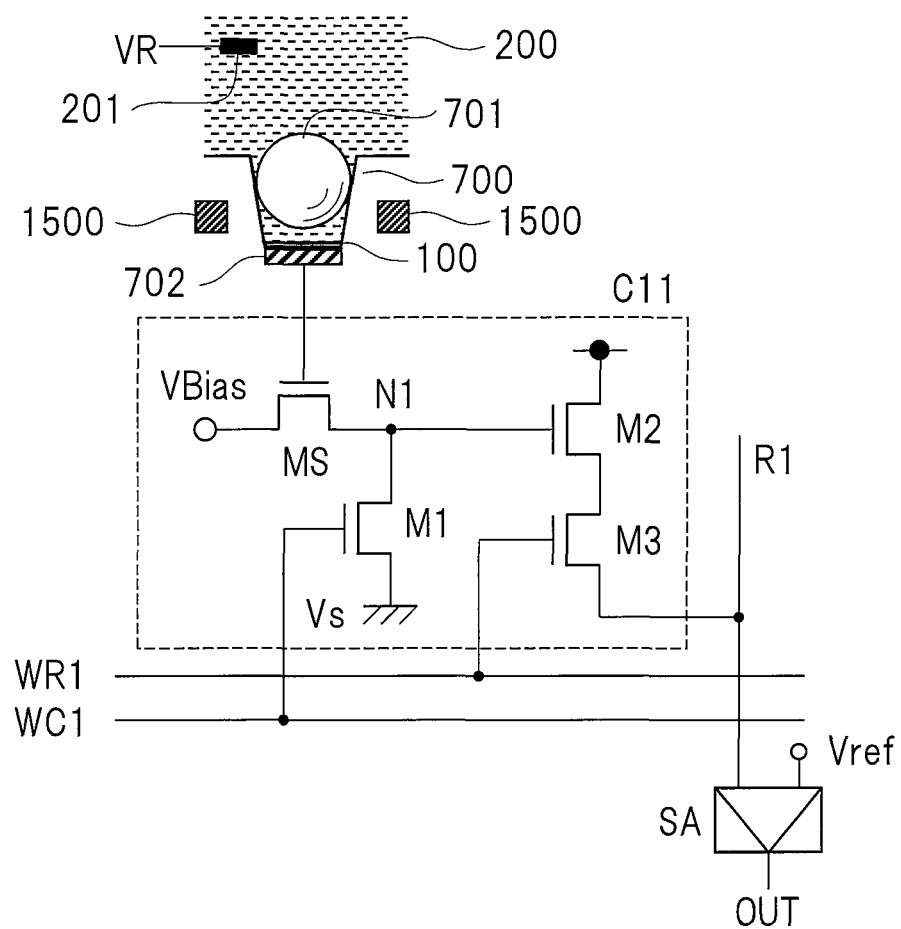
FIG. 15 is a schematic cross-sectional view of a semiconductor sensor according to a fifth embodiment.

FIG. 15 is a schematic cross-sectional view showing a configuration of a semiconductor sensor according to a fifth embodiment. This embodiment is similar to the embodiment shown in FIG. 7. A difference from the embodiment shown in FIG. 7 will be mainly described. In comparison with the embodiment shown in FIG. 7, the embodiment of FIG. 15 is provided with a heater (Heater) 1500 for use in changing the temperature of each of the wells arranged in an array form. In this embodiment, the heater 1500 is formed by a metal wire provided between the wells that are adjacent to each other. By supplying an electric current to the metal wires provided between the wells that are adjacent to each other, the metal wire generates heat to change the temperatures of the wells. This manner can achieve a device for controlling the elongation reaction itself of DNA due to a reagent. By the temperature control as described above and the cell including the highly sensitive ISFETs that are arranged in the array form, a base sequence can be obtained with higher accuracy.

Not only the DNA elongation but also the reaction of biomolecules due to a reagent generally depends on a temperature. By utilizing the characteristics, for example, a state change at an actual reaction temperature can be captured with higher sensitivity while referring to a state at a low temperature described later.

Figure 16:
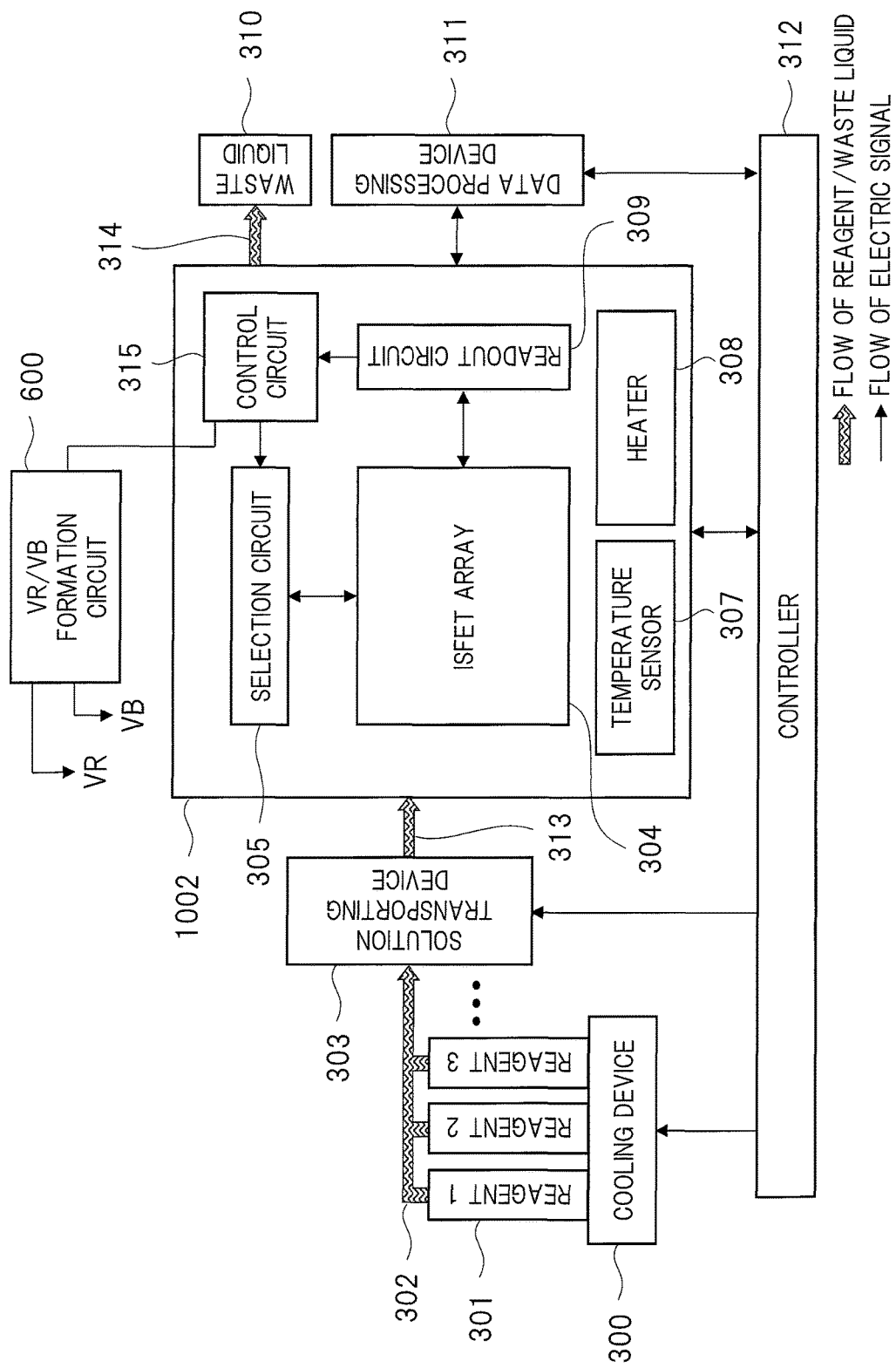
FIG. 16 is a block diagram showing a configuration of a biomolecule measuring device.

FIG. 16 is a block diagram showing a configuration of a biomolecule measuring device in which the semiconductor sensor having the heater 1500 shown in FIG. 15 is used. Since the biomolecule measuring device shown in FIG. 16 is similar to the biomolecule measuring device shown in FIG. 6, a difference will be mainly described. In comparison with the biomolecule measuring device shown in FIG. 6, an ISFET array chip (semiconductor sensor) 1002 is provided with a temperature sensor 307 and a heater control circuit 308 (heater in the drawing) for controlling the heater 1500. Based on temperature information from the temperature sensor 307, the heater control circuit 308 controls an electric current to be supplied to the heater 1500 provided between the respective wells. By the temperature sensor 307, the temperature in an actual reaction can be correctly captured, so that a detailed temperature control is achieved. Note that the temperature sensor 307 may be configured by using a semiconductor configuration.

FIG. 17(A) and FIG. 17(B) are waveform diagrams for explaining operations of the biomolecule measuring device shown in FIG. 16. In FIG. 17(A) and FIG. 17(B), a horizontal axis represents time, ands vertical axis represents a temperature change 1700, a reagent charging state 1701, and signals 1702 and 1704 from the ISFET in an order from up to down in this drawing. Moreover, FIG. 17(A) shows a case in which the injection of hot electrons as described above is not performed to the MOSFET MS of the ISFET, and FIG. 17(B) shows a case in which the above-described injection of hot electrons is performed to the MOSFET MS of the ISFET.

First, FIG. 17(A) will be described. In order to wash away the reagent used in a reaction of the previous cycle, a washing process is performed. As the washing liquid for use in this washing process, a low temperature washing liquid of, for example, 5° C. is used. After this process, a reaction reagent kept at a similar low temperature is charged thereto. Since the temperature is low in this state, for example, the DNA elongation reaction itself does not occur, or occurs with an extremely low probability even if it occurs. On the other hand, even if no reaction occurs, the reaction reagent itself also has a pH concentration. In response to this pH concentration, the ISFET outputs a constant signal 1703 (broken line). Here, this signal is referred to as a reaction reagent derived signal (BG).

Thereafter, at time to, an electric current is supplied to the heater 1500 so as to increase the temperature of each well 700 and increase the temperature of the reagent. Then, the DNA elongation reaction is caused by the reaction reagent, so that the ISFET detects the change in the hydrogen ion concentration caused by the reaction, and outputs a signal corresponding to the elongation reaction. That is, a difference between the constant signal 1703 and the signal 1702 forms an elongation signal corresponding to the elongation reaction. In the case of the ISFET having the amplifying function without the offset, this pH concentration of the reaction reagent at the low temperature and the change in the pH concentration due to the elongation reaction performed after the increase in the temperature can be detected with high sensitivity. Then, by stopping the electric current flow to the heater so as to wash away the washing liquid having the low temperature, the reaction reagent is washed away, and the temperature is decreased, so that a state ready for the next measuring process is prepared. These processes are performed repeatedly.

In this embodiment, further increase in the sensitivity as shown in FIG. 17(B) can be achieved. In FIG. 17(A), the pH concentration of the reaction reagent having the low temperature is undesirably detected as the reaction reagent derived signal (BG). For this reason, it is required to remove the detection by a succeeding stage (by a computing process of the data processing device 311 (FIG. 16) or others). Moreover, as schematically shown in FIG. 17(A), a signal caused by the reaction reagent having the low temperature is generally larger than a change caused by the elongation reaction. In an attempt to increase the sensitivity, this is also apparently as a large back ground (BG), and becomes an obstacle often. However, by the utilization of the operation for reducing the offset of the ISFET, this can be reduced.

In other words, as shown in FIG. 17(B), at time (t1) after the signal caused by the reaction reagent having the low temperature is outputted, the threshold voltage of each ISFET is changed (at time t2) by injecting the hot electrons so that this back ground (BG) does not appear in the output. At time t0 after the back ground (BG) is cancelled, the elongation reaction is performed by increasing the temperature. Then, a signal (broken line 1705) based on the back ground (BG) is reduced, and only a changed portion due to the elongation (a difference between signals 1740 and 1705) mainly appears in the ISFET signal. By using such configuration and operations, the change in the pH concentration caused by a target reaction can be detected. Generally, note that the operation of the hot electron injection is performed in the order of several tens of micro-seconds while the biomolecular reaction occurs in the order of seconds. Therefore, even when the hot electrons are injected in the middle of the measurement, no delay is caused in the overall measuring process. Moreover, it is not required to change the threshold voltage for each of the measurement in some cases by performing the setting once.

FIG. 18 is a waveform diagram showing the operation for the hot electron injection performed in FIG. 17(B) in detail. In FIG. 18, on the upper side, the waveform shown in FIG. 17(B) is shown again. On the lower side of FIG. 18, a waveform obtained by enlarging the signal 1704 from the ISFET particularly between time t1 and time t2 is shown.

The signal 1704 shown on the lower side of FIG. 18 is changed by the verifying operation. After a signal caused by the reaction reagent having the low temperature is outputted (at time t1), the injection of hot electrons (HC) and the verifying operation of the ISFET are repeated to the floating gate of the ISFET (MOSFET MS) as explained in FIG. 3. That is, (1) the hot electron injection is performed, it is checked (the verifying operation (2)) whether or not the output of the cell (ISFET) is within a predetermined range.

If it is not within the predetermined range, the hot electron injection (1) is performed, and the verifying operation (2) is repeated. On the other hand, if it is within the predetermined range, the hot electron injection is not performed. In this manner, even if the signal caused by the reaction reagent having the low temperature is different for, for example, each well of each detected base, the back ground (BG) can be cancelled to an optimal value at that time. Moreover, the reaction due to the reaction reagent having the low temperature is performed in the order of seconds. On the other hand, the hot electron injection (HC)+the verifying operation are performed in the order of several tens of micro-seconds. For this reason, even when the hot electron injection and the verifying operation are repeated 100 times, they are performed in the order of several milliseconds. That is, in the drawing, the hot electron injection (HC)+the verifying operation are shown so as to be enlarged for convenience of explanation. However, in the practical operations, these operations hardly affect the overall measurements. This embodiment can be also regarded as if the hot electron injection and the verifying operation are repeated so that not the threshold value of the ISFET but the voltage of the signal 1704 is within the predetermined range.

Sixth Embodiment

FIG. 19 is a circuit diagram showing a cell configuration according to a sixth embodiment. Since the cell configuration shown in FIG. 19 is similar to the cell configuration shown in FIG. 1, a difference will be mainly described. A cell C11 shown in FIG. 19 is provided with an analog/digital conversion circuit ADC 1900 for converting an analog value derived from an output signal of the ISFET to digital bits, and a memory circuit MEM 1901 for temporarily storing the bits. Although not shown, each of the other cells arranged in the array form also has the same configuration as that of the cell C11 shown in FIG. 19. Since each of the cells is provided with a function for reducing an offset of the ISFET and a function for amplifying the signal of the ISFET, other cause of preventing the increase in the sensitivity is observed when a signal is transmitted from these cells to a succeeding stage. In this embodiment, the output of the ISFET is directly converted to a digital signal for each of the cells, and maintained. Thus, a performance of the cells obtained by reducing the offset with the high sensitivity can be maximally brought out.

Modified Example

FIG. 20 is a circuit diagram showing a modified example of FIG. 19. In this modified example, to a plurality of cells C11 and C21, commonly-used analog/digital conversion circuit ADC 200 and memory circuit MEM 201 are provided. In this modified example, the cell C11 and the cell C21 are operated in time division. By operating them in the time division, the analog/digital conversion circuit ADC 200 and the memory circuit MEM 201 can be commonly used between the plurality of cells, so that an area can be reduced.

FIG. 21 is a waveform diagram showing operations in a case of usage of a cell according to the sixth embodiment. That is, this is a waveform diagram showing operations of a biomolecule measuring device provided with the analog/digital conversion circuit ADC for each cell or for every plurality of cells. This drawing is similar to FIG. 17(A). That is, as explained in FIG. 17(A), the reaction reagent derived signal (BG) indicating the reaction itself of the reaction reagent having the low temperature is digitalized between time t0 to time t1, and is loaded into the memory circuit MEM (data MEM0). Next, by increasing the temperature, a signal caused by a practical reaction is loaded between time t2 and time t3 (data MEM1). In this case, the signal is digitized at each of time points and is transmitted to a succeeding stage, and therefore, there is no signal degradation, and therefore, the high sensitivity performance can be maintained. Moreover, difference data (difference between MEM1 and MEM0) can be formed within the cell from a simple configuration. This manner can reduce transmission/reception of signals to/from the outside, and therefore, noise is reduced by this reduction so as to contribute the increase in the sensitivity, so that the amount of signals can be also reduced. In the drawing, note that a reference "WR1" represents a change in the voltage of the readout signal wire WR1 of the cell C11.

Seventh Embodiment

FIG. 22 is a circuit diagram showing a configuration of a semiconductor sensor according to a seventh embodiment. This embodiment is an example for aiming to further increase the sensitivity. By the plurality of embodiments described earlier, the sensitivity of each cell provided with the ISFET can be increased. Since the highly sensitive cell can be obtained, it is also desired to prepare a highly sensitive reference device used in determining the output of the cell. In this embodiment, the highly sensitive reference device is achieved by using cells having two types of well sizes.

In FIG. 22, each of the cells C11 and C12 has the same circuit configuration as that of the cell C11 shown in FIG. 13. On the other hand, the cell C11 and cell C12 are different from each other in the size of the well in which the ion sensitive layers 100 connected to the ISFETs of the cell C11 and the cell C12 are provided, respectively. That is, a well 700 to which the cell C11 is coupled has a size with the beads 701 to which the measuring molecules are adhered, and a well 700 to which the cell C12 is coupled has a dimension without the beads 701. In this case, in each of the wells 700, the well to which no beads are adhered is formed by changing the size or the shape of the well without changing the size of the ion sensitive layer 100 or others. Readout wires RCR and RCL of the cells C11 and C12 formed as described above are arranged along the paired inputs of the sense amplifier SA. By preparing such a configuration, to the paired inputs of the sense amplifier SA, a pair of the one with the beads and the one without the beads are always provided (although a state without the beads in the well to which the beads can be attached can be originally provided, this state has no contribution to the measurement). In this manner, as a reference of the sense amplifier SA, a signal from a well that performs no reaction with the biomolecular substance although it has a reaction reagent can be always obtained.

Moreover, since the well that performs a reaction with the biomolecular substance and the well that performs no reaction with the biomolecular substance although it has a reaction reagent are prepared as the pair, other factors such as a temperature can be set to almost the same condition as each other by using the output OUT of the sense amplifier SA as the reference, so that an ideal reference can be prepared.

FIG. 22 shows an example in which the opening of the well coupled to the cell C12 has a larger size than that of the opening of the well coupled to the cell C11. However, the opening of the well coupled to the cell C12 may be made smaller than the diameter of the beads 700. In this manner, the beads can be prevented from adhering to the well. Moreover, in the case as shown in FIG. 22, the beads may enter the well coupled to the cell C12. However, in the washing process, the entering beads are washed out. In FIG. 22, note that a reference numeral 1500 represents a heater.

By the plurality of embodiments described above, a highly sensitive cell having the ISFET is achieved. While exemplifying a DNA sequencer in a highly sensitive biomolecule measuring device using this cell, an embodiment of a data processing device is shown in FIG. 23(A), FIG. 23(B) and FIG. 24.

As shown in FIG. 23(A), in a conventional DNA sequencer, a highly sensitive device with a low cost is achieved by preparing chips (chip A to chip C) referred to as DNA chips that react with a specific DNA base sequence. However, in this device, when necessary diagnostic items are changed, measuring contents and ranges are also changed, and therefore, it is required to prepare the chips again.

As described in the plurality of embodiments, the array is achieved by preparing the respective ISFETs, reducing the offsets of the ISFETs, and using the plurality of cells having the amplifying function, and therefore, the highly sensitivity ISFET array with an extremely low cost can be achieved by using a semiconductor technique. A semiconductor sensor having such an array is a general-purpose sensor, and can read out any base sequence. Therefore, as shown in FIG. 23(B), a main purpose is not the readout operation itself, and it is important how to easily obtain information required for the succeeding necessary diagnostic items by the data processing device unit. In other words, for the increase and the change in the diagnostic region, rather than development of a new chip such as the DNA chip, measurements are performed by using the semiconductor sensor having the highly sensitive ISFET as described in the plurality of embodiments, and are supported by a software in the data processing device unit. The configuration described in the plurality of embodiments can reduce the development of the plurality of chips in such a DNA sequencer and others, and also cut the costs.

FIG. 24 is a block diagram showing a block configuration of a data processing device to be combined with the ISFET array described in the plurality of embodiments. An inspection method for DNA information read out is different depending on each of diagnoses. Therefore, in order to perform the method at a high speed, the data processing device is configured by a dynamic-reconfiguration high-speed matching board 2400 whose function can be dynamically changed. The output of the sequencer is stored in a sequencer output data buffer 2401. The output is compared with a reference 2406 that is updated by information from a cloud system every day by a high-speed pattern matching engine 2404. The high-speed pattern matching engine 2404 is provided with base sequences effectively used for the detection, which are also updated by the cloud system as a reference table, and performs a pattern matching process at high speed by using the same principle as that of the CAM. The board as a whole is managed by a control CPU 2405, and authentication and checking processes on trace information 2403 of data and authorized ability (authentication) of the data are performed. Moreover, an IO unit 2403 is also provided with an encoding function. The combination of the board with the inexpensive highly-sensitive ISFET array described in the embodiments as described above can achieve a device in which valuable information can be obtained at high speed and low cost from the measured data based on individual needs or the newest medical data.

In the foregoing, the invention made by the present inventors has been concretely described based on the embodiments. However, the present invention is not limited to the foregoing embodiments and various modifications and alterations can be made within the scope of the present invention. In the embodiments, the hot electron injection for changing the threshold voltage of the ISFET has been explained. However, not only the hot electrons but also hot carriers may be applicable.

EXPLANATION OF REFERENCE CHARACTERS

C11, C12, C21, C22 cell
ISFET ion sensitive field effect transistor
MS and M1 to M4 MOSFET (MOS transistor)
R1 readout wire
SA sense amplifier
Vref reference voltage
WR1 readout signal wire
WC1 offset cancel signal wire
VR control voltage
101 diffusion layer
102 gate electrode
103 to 108 wire and connecting layer
202 reference electrode

The invention claimed is:

1. A biomolecule measuring apparatus comprises a semiconductor sensor for detecting ions generated by a reaction between a biomolecular sample and a reagent,
   wherein the semiconductor sensor comprises:
      a semiconductor substrate;
      a plurality of cells arranged in an array form on the semiconductor substrate, each of the plurality of cells is configured to detect ions; and
      a plurality of readout wires arranged in the array formed by the plurality of cells,
   wherein each of the plurality of cells comprises:
      an ISFET comprising a floating gate and configured to detect a change in ion concentration;
      a first MOSFET comprising a gate configured to receive an output from the ISFET and amplify the output from the ISFET;
      a second MOSFET in series to the first MOSFET, configured to selectively transmit an output from the first MOSFET to a corresponding readout wire of the plurality of readout wires; and
      a third MOSFET in series to the ISFET, configured to generate hot electrons in the ISFET and to inject a charge to the floating gate of the ISFET,
   wherein the third MOSFET is controlled based on the output received from the ISFET, and wherein the second MOSFET and the third MOSFET are separately controlled; and
   wherein the biomolecule measuring apparatus is configured to transmit the output from the ISFET to the corresponding readout wire and determine whether a threshold voltage of the ISFET is within a predetermined range, by controlling the second MOSFET.

2. The biomolecule measuring apparatus according to claim 1,
   wherein the biomolecule measuring apparatus has a first operation mode which allows an electron tunneling current to flow from the floating gate of the ISFET in each of the plurality of cells to the semiconductor substrate.

3. The biomolecule measuring apparatus according to claim 1,
wherein the ions are generated by a first reaction between the biomolecular sample and the reagent and a second reaction different from the first reaction, and
the biomolecule measuring apparatus injects the charge to the floating gate so as to reduce a change in a threshold voltage of the ISFET caused by the ions generated by the second reaction.

4. The biomolecule measuring apparatus according to claim 3,
wherein the first reaction is caused by changing a temperature of the reagent.

5. The biomolecule measuring apparatus according to claim 1, wherein prior to the operation for injecting the charge to the floating gate of the ISFET, the biomolecule measuring apparatus performs a second operation mode for allowing an electron tunneling current to flow from the floating gate of the ISFET in each of the plurality of cells to the semiconductor substrate.

6. The biomolecule measuring apparatus according to claim 1,
wherein the ISFET and third MOSFET are formed on a common substrate.

7. A biomolecule measuring apparatus comprises a semiconductor sensor for detecting ions generated by a reaction between a biomolecular sample and a reagent,
wherein the semiconductor sensor comprises:
a semiconductor substrate;
a plurality of cells arranged in an array form on the semiconductor substrate, each of the plurality of cells is configured to detect ions; and
a plurality of readout wires arranged in the array formed by the plurality of cells,
wherein each of the plurality of cells comprises:
an ISFET comprising a floating gate and configured to detect a change in ion concentration;
a first MOSFET comprising a gate configured to receive an output from the ISFET and amplify the output from the ISFET;
a second MOSFET in series to the first MOSFET, configured to selectively transmit an output from the first MOSFET to a corresponding readout wire of the plurality of readout wires;
a third MOSFET in series to the ISFET, configured to generate hot electrons in the ISFET and to inject a charge to the floating gate of the ISFET; and,
a fourth MOSFET connected to the ISFET, configured to prevent the application of a high voltage to the first MOSFET;
wherein the third MOSFET is controlled based on the output received from the ISFET, and wherein the second MOSFET and the third MOSFET are separately controlled; and
wherein the biomolecule measuring apparatus is configured to transmit the output from the ISFET to the corresponding readout wire and determine whether a threshold voltage of the ISFET is within a predetermined range, by controlling the second MOSFET.

8. The biomolecule measuring apparatus according to claim 7,
wherein the biomolecule measuring apparatus has a first operation mode which allows an electron tunneling current to flow from the floating gate of the ISFET in each of the plurality of cells to the semiconductor substrate.

9. The biomolecule measuring apparatus according to claim 7,
wherein the ions are generated by a first reaction between the biomolecular sample and the reagent and a second reaction different from the first reaction, and
the biomolecule measuring apparatus injects the charge to the floating gate so as to reduce a change in a threshold voltage of the ISFET caused by the ions generated by the second reaction.

10. The biomolecule measuring apparatus according to claim 9,
wherein the first reaction is caused by changing a temperature of the reagent.

11. The biomolecule measuring apparatus according to claim 7, wherein prior to the operation for injecting the charge to the floating gate of the ISFET, the biomolecule measuring apparatus performs a second operation mode for allowing an electron tunneling current to flow from the floating gate of the ISFET in each of the plurality of cells to the semiconductor substrate.

12. The biomolecule measuring apparatus according to claim 7,
wherein the ISFET and third MOSFET are formed on a common substrate.

* * * * *